United States Patent
Islam et al.

(10) Patent No.: US 10,501,451 B2
(45) Date of Patent: Dec. 10, 2019

(54) SELECTIVE NR2B ANTAGONISTS

(71) Applicant: BRISTOL-MYERS SQUIBB COMPANY, Princeton, NJ (US)

(72) Inventors: Imadul Islam, Richmond, CA (US); Srinivasan Thangathirupathy, Hosur (IN); Jayakumar Sankara Warrier, Bangalore (IN); Srinivas Cheruku, Bangalore (IN); Poornima Shetty, Bangalore (IN); John E. Macor, Washington Crossing, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/767,385

(22) PCT Filed: Oct. 13, 2016

(86) PCT No.: PCT/US2016/056716
§ 371 (c)(1),
(2) Date: Apr. 11, 2018

(87) PCT Pub. No.: WO2017/066368
PCT Pub. Date: Apr. 20, 2017

(65) Prior Publication Data
US 2018/0312495 A1    Nov. 1, 2018

(30) Foreign Application Priority Data
Oct. 14, 2015 (IN) .......................... 3309/DEL/2015

(51) Int. Cl.
| | | |
|---|---|---|
| C07D 413/04 | (2006.01) | |
| C07D 413/14 | (2006.01) | |
| A61K 31/497 | (2006.01) | |
| A61K 31/4523 | (2006.01) | |
| A61P 25/24 | (2006.01) | |
| C07D 413/12 | (2006.01) | |

(52) U.S. Cl.
CPC ........ C07D 413/04 (2013.01); A61K 31/4523 (2013.01); A61K 31/497 (2013.01); A61P 25/24 (2018.01); C07D 413/12 (2013.01); C07D 413/14 (2013.01); C07B 2200/09 (2013.01)

(58) Field of Classification Search
CPC .......................... C07D 413/04; C07D 413/14
See application file for complete search history.

(56) References Cited

U.S. PATENT DOCUMENTS

| | | |
|---|---|---|
| 7,022,728 B2 | 4/2006 | Cowart et al. |
| 9,187,506 B2 | 11/2015 | Thompson, III et al. |
| 9,221,796 B2 | 12/2015 | King et al. |

FOREIGN PATENT DOCUMENTS

| | | |
|---|---|---|
| EP | 1988077 A1 | 11/2008 |
| WO | 0132615 A1 | 5/2001 |
| WO | 03035641 A1 | 5/2003 |
| WO | 2004108705 A1 | 12/2004 |
| WO | 2005035523 A1 | 4/2005 |
| WO | 2009006437 A1 | 1/2009 |
| WO | WO 2011/100585 A1 | 8/2011 |
| WO | 2015105772 A1 | 7/2015 |
| WO | 2015105929 A1 | 7/2015 |

OTHER PUBLICATIONS

Hayashi, Etsuko, et al. "Automated experimental system capturing three behavioral components during murine forced swim test." Life sciences 88.9-10 (2011): 411-417.
Menniti, Frank S., et al. "CP-101,606: An NR2B-Selective NMDA Receptor Antagonist." CNS drug reviews 4.4 (1998): 307-322.
Mutel, Vincent, et al. "In vitro binding properties in rat brain of [3H] Ro 25-6981, a potent and selective antagonist of NMDA receptors containing NR2B subunits." Journal of neurochemistry 70.5 (1998): 2147-2155.
Porsolt, R. D., A. Bertin, and M. Jalfre. "Behavioral despair in mice: a primary screening test for antidepressants." Archives internationales de pharmacodynamie et de therapie 229.2 (1977): 327-336.
Preskorn, Sheldon H., et al. "An innovative design to establish proof of concept of the antidepressant effects of the NR2B subunit selective N-methyl-D-aspartate antagonist, CP-101,606, in patients with treatment-refractory major depressive disorder." Journal of clinical psychopharmacology 28.6 (2008): 631-637.
Sanacora, Gerard, et al. "Targeting the glutamatergic system to develop novel, improved therapeutics for mood disorders." Nature reviews Drug discovery 7.5 (2008): 426-437.
Thorsteinsson, Thorsteinn, et al. "Cycloserine fatty acid derivatives as prodrugs: synthesis, degradation and in vitro skin permeability." Chemical and pharmaceutical bulletin 50.4 (2002): 554-557.
Yuan, Peixiong, et al. "Phosphodiesterase 4 inhibitors enhance sexual pleasure-seeking activity in rodents." Pharmacology Biochemistry and Behavior 98.3 (2011): 349-355.
Zarate, Carlos A., et al. "A randomized trial of an N-methyl-D-aspartate antagonist in treatment-resistant major depression." Archives of general psychiatry 63.8 (2006): 856-864.

*Primary Examiner* — Brian E McDowell
(74) *Attorney, Agent, or Firm* — Mintz Levin Cohn Ferris Glovsky and Popeo, P.C.

(57) ABSTRACT

The present disclosure provides compounds of Formula (I) and pharmaceutically acceptable salts thereof. The Formula (I) compounds are ligands for NR2B N-Methyl-D-aspartate (NMDA) receptor and thereby making them useful for the treatment of various disorders of the central nervous system.

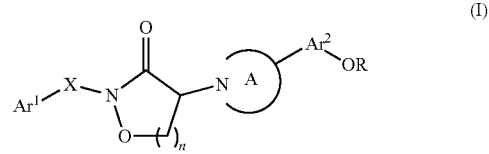

(I)

19 Claims, No Drawings

SELECTIVE NR2B ANTAGONISTS

CROSS REFERENCE TO RELATED APPLICATION

This application claims the benefit of Indian Provisional Patent Application serial number 3309/DEL/2015 filed Oct. 14, 2015 hereby incorporated by reference in its entirety.

TECHNICAL FIELD

The disclosure generally relates to compounds of formula I, including their salts, as well as compositions and methods of using the compounds. The compounds are ligands for the NR2B NMDA receptor and may be useful for the treatment of various disorders of the central nervous system.

BACKGROUND

N-Methyl-D-aspartate (NMDA) receptors are ion channels which are gated by the binding of glutamate, an excitatory neurotransmitter in the central nervous system. They are thought to play a key role in the development of a number of neurological diseases, including depression, neuropathic pain, Alzheimer's disease, and Parkinson's disease. Functional NMDA receptors are tetrameric structures primarily composed of two NR1 and two NR2 subunits. The NR2 subunit is further subdivided into four individual subtypes: NR2A, NR2B, NR2C, and NR2D, which are differentially distributed throughout the brain. Antagonists or allosteric modulators of NMDA receptors, in particular NR2B subunit-containing channels, have been investigated as therapeutic agents for the treatment of major depressive disorder (G. Sanacora, 2008, Nature Rev. Drug Disc. 7: 426-437).

The NR2B receptor contains additional ligand binding sites in addition to that for glutamate. Non-selective NMDA antagonists such as Ketamine are pore blockers, interfering with the transport of $Ca^{++}$ through the channel. Ketamine has demonstrated rapid and enduring antidepressant properties in human clinical trials as an i.v. drug. Additionally, efficacy was maintained with repeated, intermittent infusions of Ketamine (Zarate et al., 2006, Arch. Gen. Psychiatry 63: 856-864). This class of drugs, though, has limited therapeutic value because of its CNS side effects, including dissociative effects.

An allosteric, non-competitive binding site has also been identified in the N-terminal domain of NR2B. Agents which bind selectively at this site, such as Traxoprodil, exhibited a sustained antidepressant response and improved side effect profile in human clinical trials as an i.v. drug (Preskorn et al., 2008, J. Clin. Psychopharmacol., 28: 631-637, and F. S. Menniti, et al., 1998, CNS Drug Reviews, 4, 4, 307-322). However, development of drugs from this class has been hindered by low bioavailability, poor pharmacokinetics, and lack of selectivity against other pharmacological targets including the hERG ion channel. Blockade of the hERG ion channel can lead to cardiac arrythmias, including the potentially fatal Torsades de pointe, thus selectivity against this channel is critical. Thus, in the treatment of major depressive disorder, there remains an unmet clinical need for the development of effective NR2B-selective negative allosteric modulators which have a favorable tolerability profile.

NR2B receptor antagonists have been disclosed in publications WO01/32615, WO 03/035641, WO2005/035523, WO 2009/006437, and EP1988077.

The disclosure provides technical advantages, for example, the compounds are novel and are ligands for the NR2B receptor and may be useful for the treatment of various disorders of the central nervous system. Additionally, the compounds provide advantages for pharmaceutical uses, for example, with regard to one or more of their mechanism of action, binding, inhibition efficacy, target selectivity, solubility, safety profiles, or bioavailability.

SUMMARY

In a first embodiment, the disclosure provides a compound of the formula I

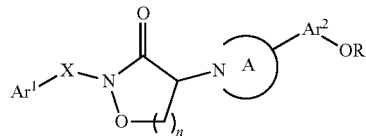

where:
Ar$^1$ is phenyl and is substituted with 0-3 substituent selected from cyano, halo, alkyl, haloalkyl and haloalkoxy;
Ar$^2$ is phenyl, pyridinyl or pyrimidinyl, and is substituted with 1 OR substituent and with 0-2 halo or alkyl substituents;
R is hydrogen or a prodrug moiety selected from the group consisting of alkyl esters, amino acid esters, alkoxy esters, phosphonic acids, phosphonic alkyl esters, alkoxyphosphononate acid, alkoxyphosphonate alkyl esters, alkyl carabamates, amino acid carbamates, alkyl phosporamidates, aryl phosphoramidates, and sulfamates;
X is a bond or $C_1$-$C_3$ alkylene;
n is 1 or 2;
ring A is piperidine, piperazine and is substituted with 0-1 halo substituents;
or a pharmaceutically acceptable salt thereof.

DESCRIPTION

It will be understood that any given exemplary embodiment can be combined with one or more additional exemplary embodiments.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion. "Halo" includes fluoro, chloro, bromo, and iodo. "Haloalkyl" and "haloalkoxy" include all halogenated isomers from monohalo to perhalo. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R. The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc. Some Formula I compounds contain at least one asymmetric carbon atom, an example of which is shown below. The invention includes all stereoisomeric forms of the compounds, both mixtures and separated isomers. Mixtures of stereoisomers can be separated into individual isomers by methods known in the art. The compounds include all tautomeric forms.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The abbreviations used in the present application are well-known to those skilled in the art.

In a first aspect, a compound of the formula I

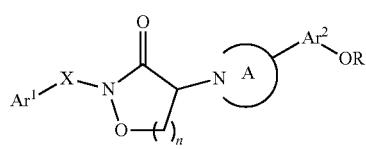

where:
Ar$^1$ is phenyl and is substituted with 0-3 substituent selected from cyano, halo, alkyl, haloalkyl and haloalkoxy;
Ar$^2$ is phenyl, pyridinyl or pyrimidinyl, and is substituted with 1 OR substituent and with 0-2 halo or alkyl substituents;
R is hydrogen or a prodrug moiety selected from the group consisting of alkyl esters, amino acid esters, alkoxy esters, phosphonic acids, phosphonic alkyl esters, alkoxyesters, phosphononate acid, alkoxyphosphonate alkyl esters, alkyl carabamates, amino acid carbamates, alkyl phosporamidates, aryl phosphoramidates, and sulfamates;
X is a bond or $C_1$-$C_3$ alkylene;
n is 1 or 2;
ring A is piperidine, piperazine and is substituted with 0-1 halo substituents;
or a pharmaceutically acceptable salt thereof.

In a second embodiment of the first aspect A compound of claim 1 where Ar$^1$ is phenyl and is substituted with 0-1 substituent selected from halo and alkyl; Ar$^2$ is phenyl, pyridinyl or pyrimidinyl, and is substituted with 1 OR substituent and with 0-2 halo or alkyl substituents; R is hydrogen; X is a bond or $C_1$-$C_3$ alkylene; n is 1 or 2; ring A is piperidine, piperazine and is substituted with 0-1 halo substituents; or a pharmaceutically acceptable salt thereof.

In a third embodiment of the first aspect A compound of claim 2 where Ar$^1$ is phenyl and is substituted with 0-1 substituent selected from halo and alkyl; Ar$^2$ is phenyl or pyridinyl, and is substituted with 1 OR substituent and with 0-1 halo substituents; R is hydrogen; X is a methylene; n is 1 or 2; ring A is piperidine or piperazine and is substituted with 0-1 halo substituents; or a pharmaceutically acceptable salt thereof.

In a fourth embodiment of the first aspect A compound of claim 1 where n is 1 and ring A is piperazine or piperidine substituted with 0-1 fluoro.

In a fifth embodiment of the first aspect A compound of claim 1 where Ar$^1$ is phenyl substituted with 0-1 substituents selected from chloro, fluoro and methyl.

In a sixth embodiment of the first aspect A compound of claim 1 where Ar$^2$ is selected from

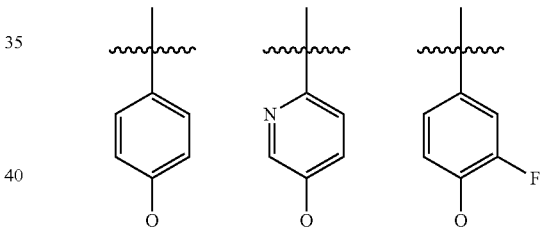

In a seventh embodiment of the first aspect A compound of claim 1 where X is methylene.

In an eighth embodiment of the first aspect, a compound of formula I where n is 1 and ring A is piperazine or piperidine substituted with 0-1 fluoro.

In a ninth embodiment of the first aspect, a compound of formula I where Ar$^1$ is phenyl substituted with 0-1 substituents selected from chloro, fluoro and methyl.

In a third embodiment of the first aspect, a compound of formula I where Ar$^2$ is selected from

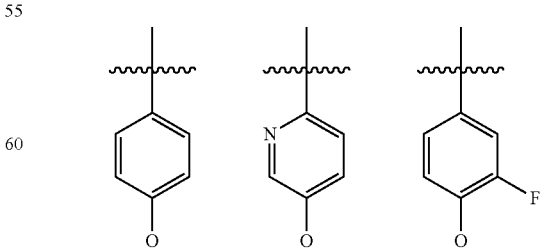

In a tenth embodiment of the first aspect, a compound of formula I where X is methylene.

In an eleventh embodiment of the first aspect, the compound of formula I is:

-continued

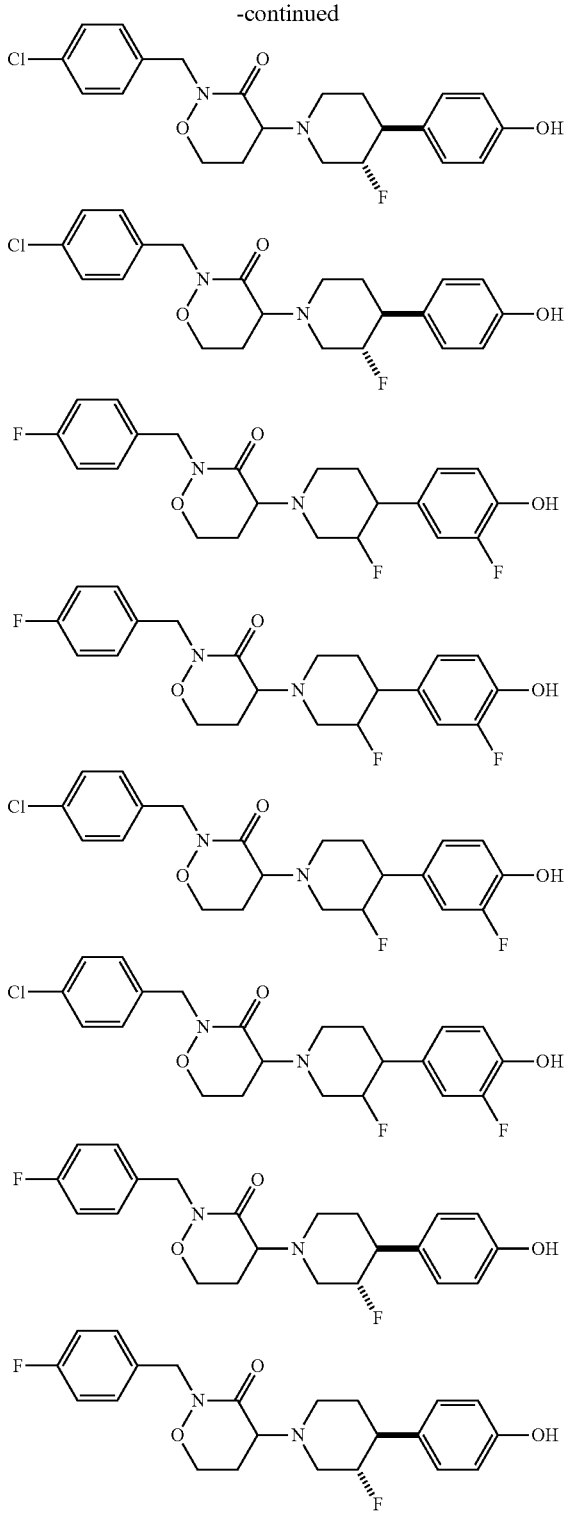

or a pharmaceutically acceptable salt thereof.

In a second aspect, a pharmaceutical composition comprising a compound of formula I or a pharmaceutically acceptable salt thereof and a pharmaceutically acceptable carrier.

In a third aspect, a method for the treatment of depression, Alzheimer's disease, neuropathic pain, or Parkinson's disease, which comprises administering to a patient a therapeutically affective amount of a compound of formula I.

In a second embodiment of the third aspect, the compound of formula I is directed to the treatment of depression.

In a third embodiment of the third aspect, the compound of formula I is directed to the treatment of Alzheimer's disease.

In a fourth embodiment of the third aspect, the compound of formula I is directed to the treatment of neuropathic pain.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present disclosure may be prepared using the reactions and techniques described in this section, as well as, other synthetic methods known to those of ordinary skill in the art. The reactions are performed in solvents appropriate to the reagents and materials employed and suitable for the transformation being affected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

In a preferred embodiment of the invention, the synthesis of the compounds of instant disclosure can be set forth in the following schematic representations—Scheme 1 to scheme 3.

Scheme 1

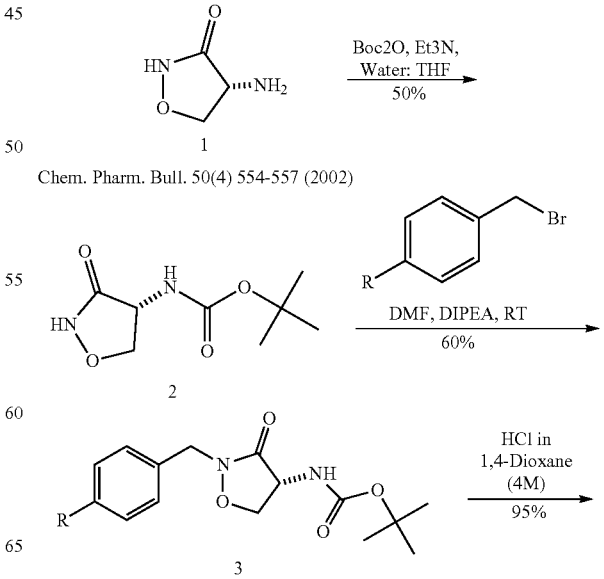

Chem. Pharm. Bull. 50(4) 554-557 (2002)

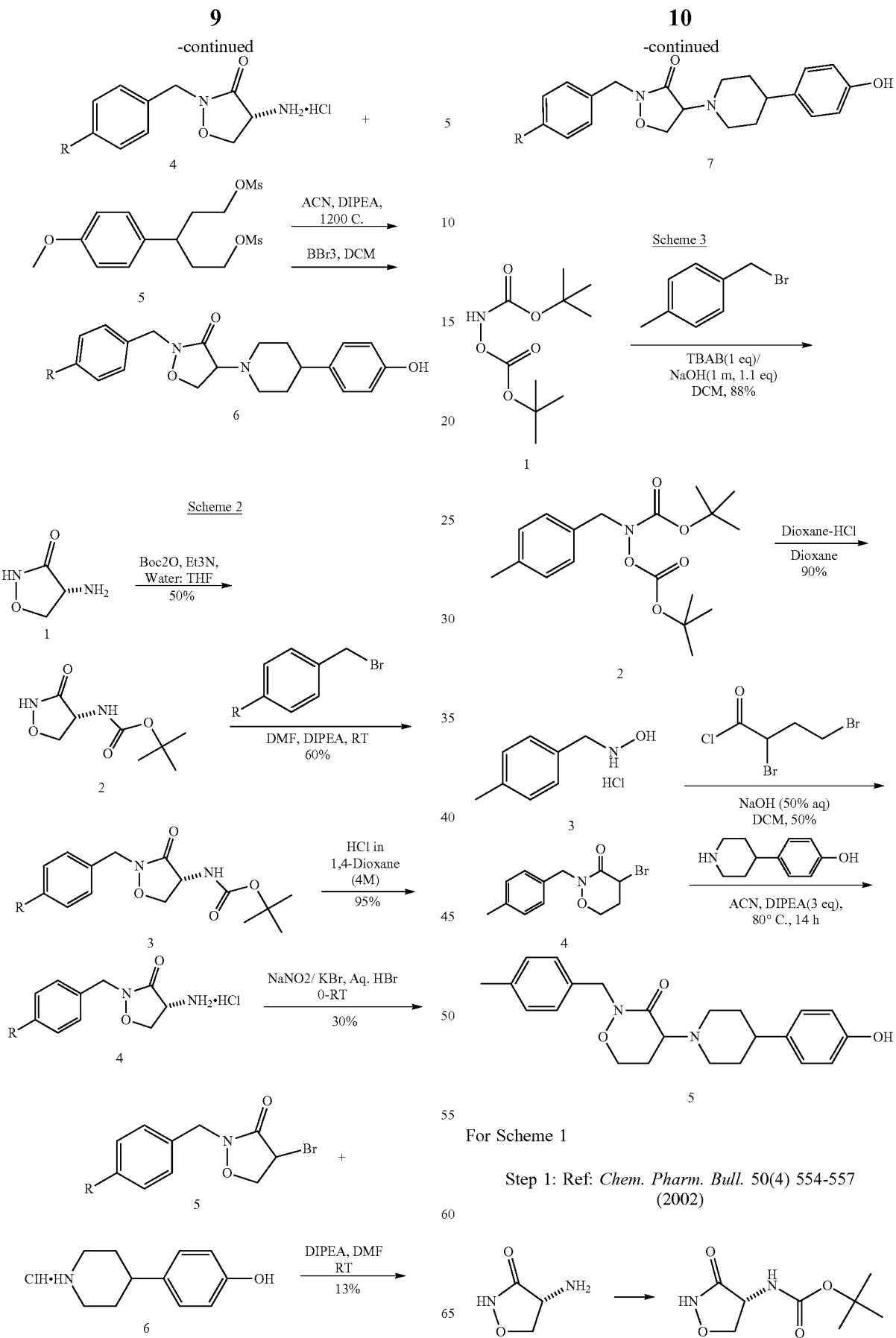

To a stirred solution of (R)-4-aminoisoxazolidin-3-one (2.00 g, 19.59 mmol) in THF (30 mL) and Water (10 mL) was added TRIETHYLAMINE (3.28 mL, 23.51 mmol) and Boc$_2$O (4.55 mL, 19.59 mmol) at RT. The reaction mixture was stirred at RT for 12 h. The completion of the reaction was monitored by LCMS. The reaction mixture was concentrated and was purified by ISCO using 12 g silica gel column, the product was eluted at 55% ethyl acetate in pet ether to get (R)-tert-butyl (3-oxoisoxazolidin-4-yl)carbamate (3 g, 14.84 mmol, 76% yield) as off white solid.

LCMS: Buffer:10 mM Ammonium Acetate pH −5 adjusted with HCOOH, Mobile phase A:Buffer:ACN (95:5), Mobile phase B:Buffer:ACN (5:95), Method:% B: 0min-5%:1.1 min-95%:1.7 min-95% Column Name: Acquity BEH C18 (2.1×50 mm) 1.7 u Method:C:\MassLynx, Flow: 0.8 ml/min, RT-0.54 min, M(+1)−147 (t-Butyl cleaved mass).

Step 2a: (R)-tert-butyl (2-(4-fluorobenzyl)-3-oxoisoxazolidin-4-yl)carbamate

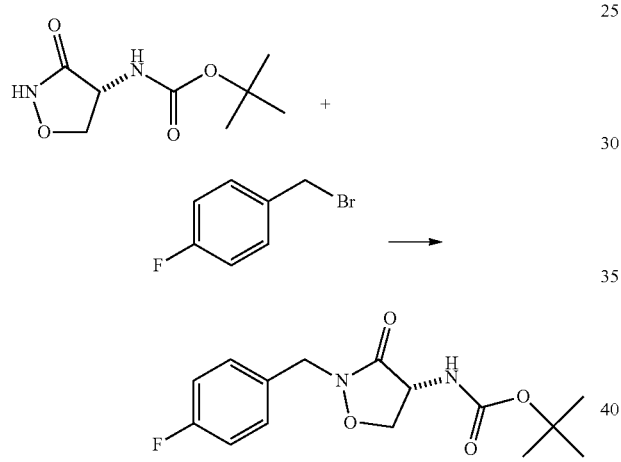

To a stirred solution of (R)-tert-butyl (3-oxoisoxazolidin-4-yl)carbamate (0.5 g, 2.473 mmol) in DMF (5 mL) was added DIPEA (1.296 mL, 7.42 mmol) and 1-(bromomethyl)-4-fluorobenzene (0.561 g, 2.97 mmol) at RT. The reaction mixture was stirred at RT for 12 h. The completion of the reaction was monitored by LCMS. The reaction mixture was concentrated and was taken for column purification. The crude product was purified by ISCO using 12 g silica gel column, the product was eluted with 35% ethylacetate in hexane to get (R)-tert-butyl (2-(4-fluorobenzyl)-3-oxoisoxazolidin-4-yl)carbamate (0.35 g, 1.128 mmol, 45.6% yield) as off white solid.

LCMS: Buffer:10 mM AmmoniumAcetate pH −5 adjusted with HCOOH, Mobile phase A:Buffer:ACN (95:5), Mobile phase B:Buffer:ACN (5:95), Method:% B: 0min-5%:1.1 min-95%:1.7 min-95% Column Name: Acquity BEH C18 (2.1×50 mm) 1.7 u Method:C:\MassLynx, Flow: 0.8 ml/min, RT-0.93 min, M(+1)−255 (t-Butyl cleaved mass).

1H NMR: 400 MHz, DMSO-d6: δ 1.40 (s, 9H), 3.92-4.06 (m, 1H), 4.46-4.51 (m, 2H), 4.60-4.71 (m, 3H), 7.11-7.21 (m, 2H), 7.33-7.36 (m, 2H), 7.51 (d, J=8.40 Hz, 1H).

Step 2b: (R)-tert-butyl (2-(4-methylbenzyl)-3-oxoisoxazolidin-4-yl)carbamate

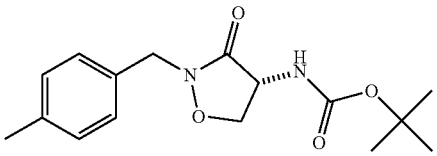 [SMILES: Cc1ccc(CN2OC[C@@H](NC(=O)OC(C)(C)C)C2=O)cc1]

To a stirred solution of (R)-tert-butyl (3-oxoisoxazolidin-4-yl)carbamate (0.5 g, 2.473 mmol) in DMF (5 mL) was added DIPEA (1.296 mL, 7.42 mmol) and 1-(bromomethyl)-4-methylbenzene (0.549 g, 2.97 mmol) at RT. The reaction mixture was stirred at RT for 12 hrs. The completion of the reaction was monitored by LCMS. The reaction mixture was concentrated to remove DMF and the crude 1.1 g as such was taken for column purification. The crude product was purified by ISCO using 12 g silica gel column and was eluted with 21% ethylacetate in pet ether to get (R)-tert-butyl (2-(4-methylbenzyl)-3-oxoisoxazolidin-4-yl)carbamate (0.3 g, 0.979 mmol, 39.6% yield) as off white solid.

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, RT-2.156 min, M(−1)−305.

1H NMR: 400 MHz, DMSO-d6: δ 1.40-0.00 (m, 9H), 2.29 (s, 3H), 3.85-3.90 (m, 1H), 4.44-4.49 (m, 1H), 4.55-4.65 (m, 3H), 7.14-7.20 (m, 4H), 7.49 (d, J=8.80 Hz, 1H).

Chiral screening: Injection Volume: 10, Co-Solvent: 0.3% DEA in Methanol, Column: Chiralpak AD H (250×4.6)mm 5 u, Column Temperature: 23, Total Flow: 3, CO2 Flow Rate: 1.95, Co-Solvent Flow Rate: 1.05, Co-Solvent %: 35, Back Pressure: 102, RT-3.58 min, 93% pure.

Step 3a: (R)-4-amino-2-(4-fluorobenzyl)isoxazolidin-3-one.hydrochloride

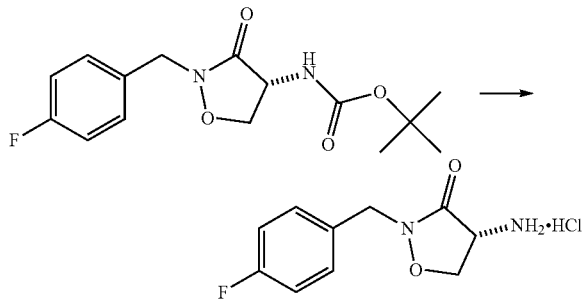

To a stirred solution of (R)-tert-butyl (2-(4-fluorobenzyl)-3-oxoisoxazolidin-4-yl)carbamate (0.4 g, 1.289 mmol) in 1,4-Dioxane (10 mL) was added 4M HCl in 1,4-Dioxane (2 mL, 8.00 mmol) at RT. The reaction mixture was stirred at RT for 2 h. Major desired product mass by LCMS, the reaction mixture was concentrated to get (R)-4-amino-2-(4-fluorobenzyl)isoxazolidin-3-one hydrochloride (0.25 g, 1.014 mmol, 79% yield) as off white solid.

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, RT-1.681 min, M(+1)−211.

1H NMR: 400 MHz, DMSO-d6: δ 4.22 (t, J=19.60 Hz, 1H), 4.56-4.81 (m, 4H), 7.18-7.24 (m, 2H), 7.36-7.41 (m, 2H), 9.03 (s, 3H).

Step 3b: (R)-4-amino-2-(4-methylbenzyl)isoxazolidin-3-one, HCl

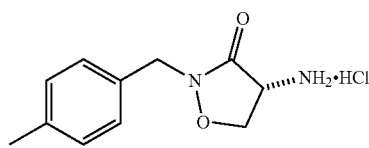

To a stirred solution of (R)-tert-butyl (2-(4-methylbenzyl)-3-oxoisoxazolidin-4-yl)carbamate (0.25 g, 0.816 mmol) in 1,4-Dioxane (5 mL) was added 4M HCl in 1,4-Dioxane(4M) (2 mL, 8.00 mmol) at RT. The reaction mixture was stirred at RT for 2 h. Major desired product mass by LCMS. The completion of the reaction was monitored by LCMS. The reaction mixture was concentrated under vaccum to get (R)-4-amino-2-(4-methylbenzyl)isoxazolidin-3-one, HCl (0.18 g, 0.742 mmol, 91% yield) as off white solid.

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, RT-1.755 min, M(+1)–207.

1H NMR:400 MHz, DMSO-d6: δ 2.30 (s, 3H), 4.16-4.20 (m, 1H), 4.57-4.65 (m, 2H), 4.69-4.70 (m, 2H), 7.17-7.23 (m, 5H), 8.96 (bs, 3H).

Synthesis of 3-(4-methoxyphenyl)pentane-1,5-diyl dimethanesulfonate

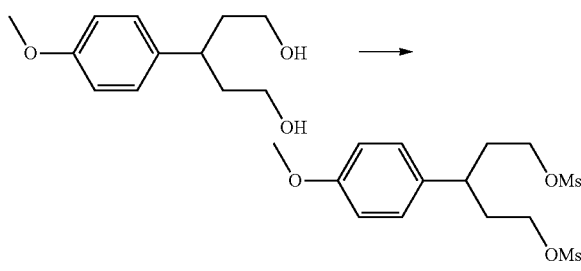

To a stirred solution of 3-(4-methoxyphenyl)pentane-1,5-diol (0.8 g, 3.80 mmol) in DCM (10 mL) was added PYRIDINE (0.923 mL, 11.41 mmol) at 0° C. The reaction mixture was stirred at RT for 15 minutes and was added Mesyl-Cl (0.652 mL, 8.37 mmol) at 0° C. and stirred at RT for 12 h. The reaction mixture was added water 100 ml, the product was extracted with DCM (3*50 mL), the combined organic layer was dried over anhydrous sodium sulphate, filtered and concentrated to get brown crude material 1.5 g. The crude was purified by isco using 12 g silica gel column, the product was eluted with 25% ethylacetate in hexane to get 3-(4-methoxyphenyl)pentane-1,5-diyl dimethanesulfonate (0.1 g, 0.273 mmol, 7.17% yield) as colorless gummy.

1H NMR: 400 MHz, DMSO-d6: δ 1.91-2.10 (m, 4H), 2.78-2.82 (m, 1H), 3.10 (s, 6H), 3.73 (s, 3H), 3.88-3.94 (m, 2H), 4.01-4.06 (m, 2H), 6.90 (d, J=8.40 Hz, 2H), 7.18 (d, J=8.40 Hz, 2H).

For Scheme 2:

Step 1a:
4-bromo-2-(4-fluorobenzyl)isoxazolidin-3-one

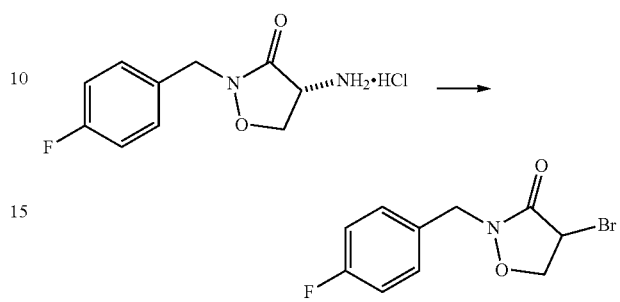

To a stirred solution of KBr (1.351 g, 11.35 mmol) and HBr in water (3 mL, 22.10 mmol) in Water (7 mL) was cooled to 0° C. temperature was added (R)-4-amino-2-(4-fluorobenzyl)isoxazolidin-3-one, HCl (0.7 g, 2.84 mmol) after 10 min, the reaction mixture was added SODIUM NITRITE (0.431 g, 6.24 mmol) in water(2 mL) slowly drop wise at 0° C. The reaction mixture was stirred at RT for 1 h. The reaction mixture was added 10% sodium bicarbonate solution (10 mL), the product was extracted with ethyl acetate (3*10 mL), the combined organic layer was dried over anhydrous sodium sulphate, filtered and concentrated to get crude 0.8 g. The crude was purified by ISCO using 12 g silica gel column, the product was eluted with 35% ethyl acetate in pet ether to get 4-bromo-2-(4-fluorobenzyl)isoxazolidin-3-one (0.3 g, 0.876 mmol, 30.9% yield) as colorless gummy material.

LCMS: Buffer:10 mM AmmoniumAcetate pH −5 adjusted with HCOOH, Mobile phase A:Buffer:ACN (95:5), Mobile phase B:Buffer:ACN (5:95), Method:% B: 0min-5%:1.1 min-95%:1.7 min-95% Column Name: Acquity BEH C18 (2.1×50 mm) 1.7 u Method:C:\MassLynx, Flow: 0.8 ml/min, RT-0.84 min, M(+1)–274.

1H NMR: 400 MHz, DMSO-d6: δ 4.44-4.47 (m, 1H), 4.63-4.68 (m, 1H), 4.73 (d, J=4.40 Hz, 2H), 5.08-5.10 (m, 1H), 7.18-7.23 (m, 2H), 7.34-7.38 (m, 2H).

Step 1b:
4-bromo-2-(4-methylbenzyl)isoxazolidin-3-one

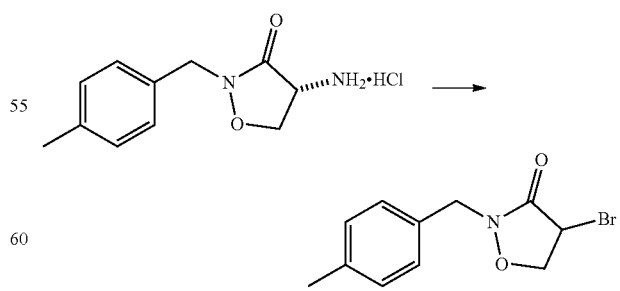

To a stirred solution of KBr (1.961 g, 16.48 mmol) and HBr (4 ml, 73.7 mmol) in Water (10 mL) was cooled to 0° C. temperature was added (R)-4-amino-2-(4-methylbenzyl)isoxazolidin-3-one, HCl (1 g, 4.12 mmol) after 10 min, the reaction mixture was added SODIUM NITRITE (0.625 g, 9.06 mmol) in water(2 mL) slowly drop wise at 0° C. The reaction mixture was stirred at RT for 1 h. The completion of the reaction was monitored by LCMS. The reaction mixture was added 10% sodium bicarbonate solution (10 mL), the product was extracted with ethyl acetate (3*10 mL), the combined organic layer was dried over anhydrous sodium sulphate, filtered and concentrated to get crude 1.1 g. The crude compound was purified by ISCO using 12 g silica gel column, the product was eluted with 15% ethyl acetate in pet ether to get 4-bromo-2-(4-methylbenzyl)isoxazolidin-3-one (0.5 g, 1.851 mmol, 44.9% yield) as colorless gummy material.

1H NMR: 400 MHz, DMSO-d6: δ 2.04 (s, 3H), 4.42-4.46 (m, 2H), 4.60-4.68 (m, 3H), 5.05-5.10 (m, 2H), 7.18 (d, J=2.40 Hz, 4H).

For Scheme 3:

Step 1a: Synthesis of tert-butyl (tert-butoxycarbonyl)oxy(4-methylbenzyl)carbamate

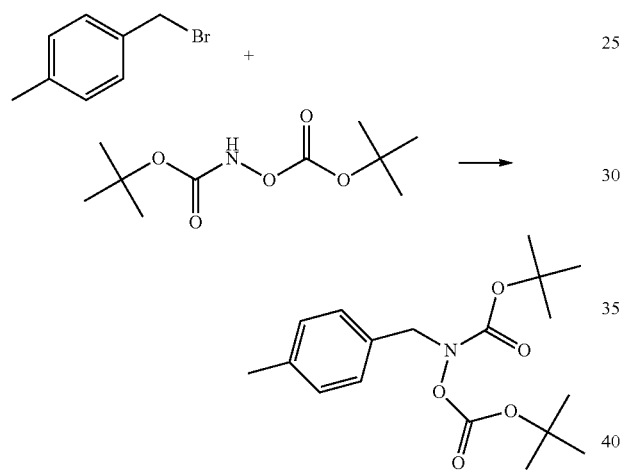

To a solution of tert-butyl (tert-butoxycarbonyl)oxycarbamate (0.347 g, 1.486 mmol) and 1-(bromomethyl)-4-methylbenzene (0.25 g, 1.351 mmol) in DCM (5 mL) was added NaOH (1.486 mL, 1.486 mmol) followed by tetrabutylammonium bromide (0.435 g, 1.351 mmol) and stirred at RT for overnight. The completion of the reaction was monitored by TLC. The reaction mixture was added water (50 mL) and extracted with DCM (2×25 mL), the combined organic layer was dried over sodium sulphate and concentrated under reduced pressure to get tert-butyl (tert-butoxycarbonyl)oxy(4-methylbenzyl)carbamate (0.4 g, 1.162 mmol, 86% yield) as colorless liquid.

1H NMR: 400 MHz, DMSO-d6: δ 1.42 (s, 18H), 2.29 (s, 3H), 4.66 (s, 2H), 7.16 (s, 4H).

Step 1b: Synthesis of tert-butyl (tert-butoxycarbonyl)oxy(4-chlorobenzyl)carbamate

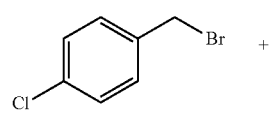

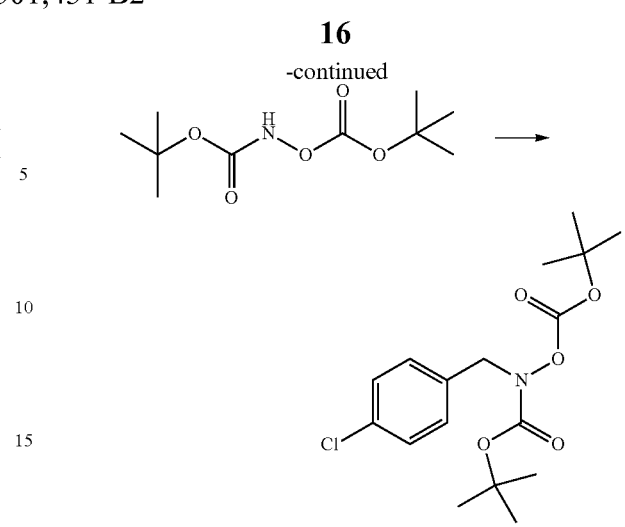

To a solution of tert-butyl (tert-butoxycarbonyl)oxycarbamate (2.497 g, 10.71 mmol) and 1-(bromomethyl)-4-chlorobenzene (2 g, 9.73 mmol) in DCM (25 mL) was added NaOH (10.71 mL, 10.71 mmol) followed by TETRABUTYLAMMONIUM BROMIDE (3.14 g, 9.73 mmol) stirred at RT for overnight. The reaction mixture was added water (100 mL) and the product was extracted with ethylacetate (3*100 mL), the combined organic layer was dried over anhydrous sodium sulphate, filtered and concentrated to get crude 5.4 g. The crude was purified by ISCO using 40 g silica gel column, the product was eluted with 10% ethylacetate in pet ether to get tert-butyl (tert-butoxycarbonyl)oxy(4-chlorobenzyl)carbamate (3.1 g, 8.66 mmol, 89% yield) as colorless gummy material.

1H NMR: 300 MHz, DMSO-d6: δ 1.42 (s, 18H), 4.69 (s, 2H), 7.16-7.22 (m, 2H), 7.31-7.34 (m, 2H).

Step 1c: Synthesis of tert-butyl (tert-butoxycarbonyl)oxy(4-fluorobenzyl)carbamate

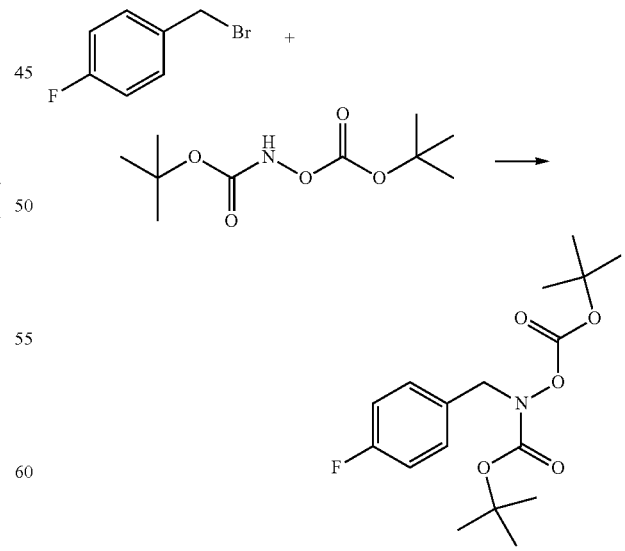

To a solution of tert-butyl (tert-butoxycarbonyl)oxycarbamate (2.71 g, 11.64 mmol) and 1-(bromomethyl)-4-fluorobenzene (2 g, 10.58 mmol) in DCM (25 mL) was added NaOH (11.64 mL, 11.64 mmol) followed by TETRABU-TYLAMMONIUM BROMIDE (3.41 g, 10.58 mmol) stirred at RT for overnight. The reaction mixture was added water (100 mL) and the product was extracted with ethyl acetate (3*100 mL), the combined organic layer was dried over anhydrous sodium sulphate, filtered and concentrated to get crude 5.5 g. The crude was purified by ISCO using 40 g silica gel column, the product was eluted with 10% ethyl acetate in pet ether to get tert-butyl (tert-butoxycarbonyl)oxy(4-fluorobenzyl)carbamate (3.1 g, 8.99 mmol, 85% yield) as colorless gummy material.

1H NMR: 300 MHz, DMSO-d6: δ 1.42 (s, 18H), 4.69 (s, 2H), 7.16-7.22 (m, 2H), 7.31-7.34 (m, 2H).

Step 2a: Synthesis of N-(4-methylbenzyl)hydroxylamine,HCl

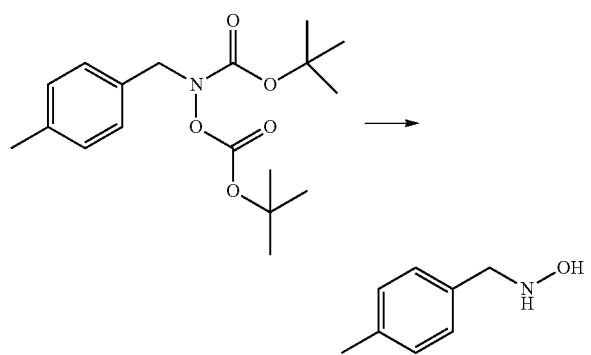

To a solution of tert-butyl (tert-butoxycarbonyl)oxy(4-methylbenzyl)carbamate (0.25 g, 0.741 mmol) in 1,4-Dioxane (3 mL) was added 4M HCl in Dioxane (3 mL, 12.00 mmol) and stirred at RT for overnight. The completion of the reaction was monitored by TLC. The reaction mixture was concentrated under reduced pressure. Then washed with ethyl acetate, filtered and dried to get N-(4-methylbenzyl)hydroxylamine, HCl (0.13 g, 0.864 mmol, 97% yield) as off white solid.

1H NMR: 400 MHz, DMSO-d6: δ 2.32 (s, 3H), 4.25 (s, 2H), 7.22 (d, J=8.00 Hz, 2H), 7.39 (d, J=8.00 Hz, 2H), 10.91 (s, 1H), 11.62 (s, 1H).

Step 2b: Synthesis of N-(4-chlorobenzyl)hydroxylamine,HCl

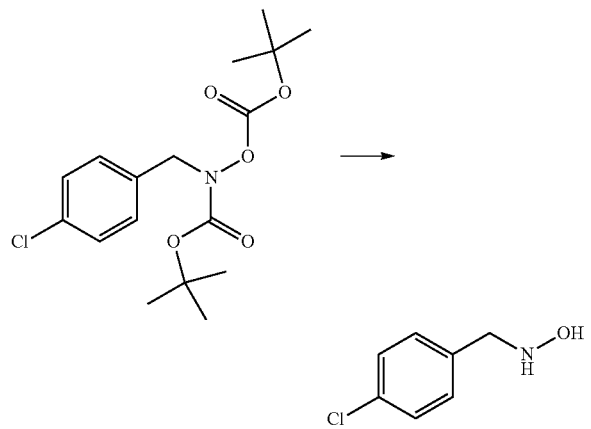

To a stirred solution of tert-butyl (tert-butoxycarbonyl)oxy(4-chlorobenzyl)carbamate (4 g, 11.18 mmol) in 1,4-Dioxane (30 mL) was added 4M HCl in 1,4-Dioxane (15 mL, 11.18 mmol) at RT. The reaction mixture was stirred at RT for 18 h. The reaction mixture was concentrated to get N-(4-chlorobenzyl)hydroxylamine, HCl (1.8 g, 9.28 mmol, 83% yield) as off white solid.

1H NMR: 400 MHz, DMSO-d6: δ 4.33 (d, J=6.40 Hz, 2H), 7.49-7.52 (m, 2H), 7.54-7.57 (m, 2H), 10.97 (s, 1H), 11.80 (s, 2H).

Step 2c: Synthesis of N-(4-fluorobenzyl)hydroxylamine, HCl

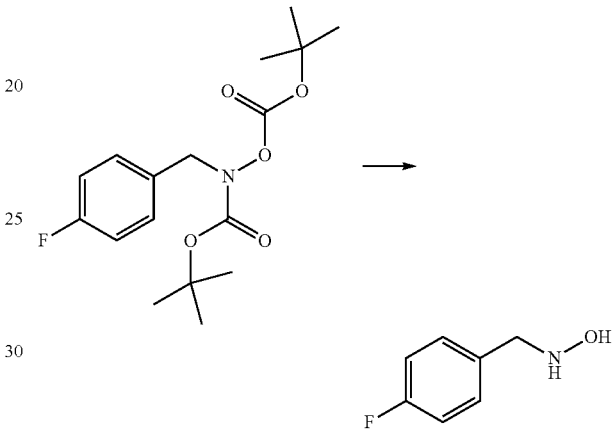

To stirred solution of tert-butyl (tert-butoxycarbonyl)oxy(4-fluorobenzyl)carbamate (4 g, 11.72 mmol) in 1,4-Dioxane (30 mL) was added 4M HCl in 1,4-Dioxane (15 mL, 11.72 mmol) at RT. The reaction mixture was stirred at RT for 12 h. The reaction mixture was concentrated to get N-(4-fluorobenzyl)hydroxylamine, HCl (1.5 g, 8.45 mmol, 72.1% yield) as off white solid.

1H NMR: 400 MHz, DMSO-d6: δ 4.31 (s, 2H), 7.23-7.29 (m, 2H), 7.54-7.58 (m, 2H), 10.92 (s, 1H), 11.67 (s, 2H).

Step 3a: Synthesis of 4-bromo-2-(4-methylbenzyl)-1,2-oxazinan-3-one

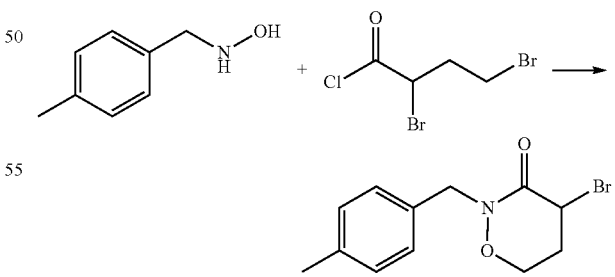

To a solution of N-(4-methylbenzyl)hydroxylamine, HCl (0.15 g, 0.864 mmol) in DCM (5 mL) and NaOH (0.038 g, 0.950 mmol) in Water (1 mL) cooled to 5° C. was added 2,4-dibromobutanoyl chloride (0.126 mL, 0.950 mmol) drop wise and additional 50% aqueous NaOH (0.038 g, 0.950 mmol) solution at 5° C. The reaction mixture was stirred at 5° C. for 2 hrs. Then again 50% aqueous NaOH (0.038 g, 0.950 mmol) solution was added at 5° C. and the reaction mixture was stirred at RT for 16 h. The completion of the reaction was monitored by LCMS. The reaction mass was diluted with water (25 mL) and the product was extracted with DCM (2×25 mL), the combined organic layer was dried over sodium sulphate, filtered and concentrated under reduced pressure to get crude 0.2 g. The crude was purified by ISCO (15% EA:Hexane, 12 g silica gel column) to get 4-bromo-2-(4-methylbenzyl)-1,2-oxazinan-3-one (0.07 g, 0.224 mmol, 26.0% yield) as colorless gummy material.

LCMS: Column-Ascentis Express C18 (50×2.1 mm-2.7 μm), Mphase A: 2% ACN-98% H20-10 mM NH4C00H, Mphase B: 98% ACN-2% H20-10 mM NH4C00H, Flow=1 ML/MIN Time:% B::0.0:0.0::1.7:100.0::3.4:100.0, RT:1.89 min; (M+H):284.

1H NMR: 300 MHz, DMSO-d6: δ 2.19-2.26 (m, 1H), 2.29 (s, 3H), 2.65-2.72 (m, 1H), 3.98-4.14 (m, 1H), 4.72 (s, 2H), 4.91-4.95 (m, 1H), 7.14-7.21 (m, 4H).

Step 3b: Synthesis of 4-bromo-2-(4-chlorobenzyl)morpholin-3-one

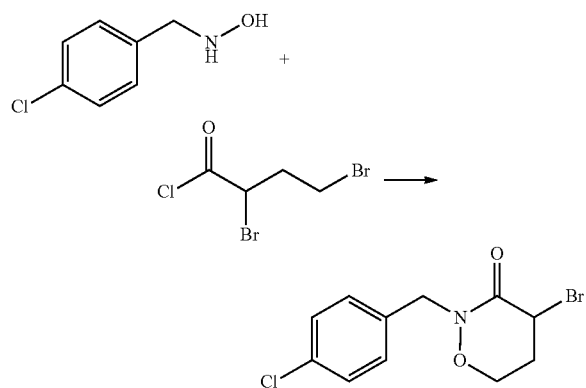

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, Time:% B::0.0:0.0::1.7:100.0::3.0:100.0::3.2:0.0, RT-2.148 min, (M+1)–304.

Step 3c: Synthesis of 4-bromo-2-(4-fluorobenzyl)morpholin-3-one

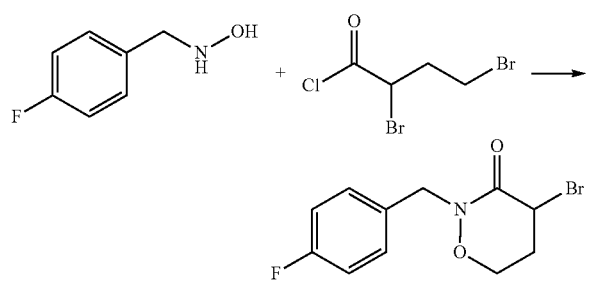

LCMS: Column-Ascentis Express C18 (50×2.1 mm-2.7 μm), Mphase A: 10 mM NH4C00H

Mphase B: CAN, Flow=1 ML/MIN, Time:% B::0.0:50:: 1.7:100.0::4.0:100.0,

RT-2.123 min, (M+1)–288.

Example 1 (P1 & P2)

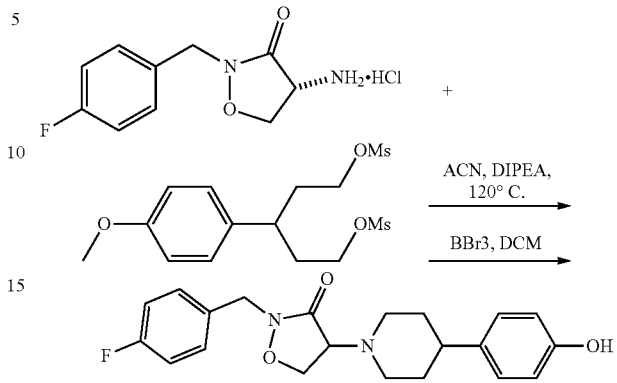

To a stirred solution of (R)-4-amino-2-(4-fluorobenzyl)isoxazolidin-3-one (0.092 g, 0.437 mmol) in ACN (2 mL) was added DIPEA (0.381 mL, 2.183 mmol) and 3-(4-methoxyphenyl)pentane-1,5-diyl dimethanesulfonate (0.16 g, 0.437 mmol) at RT. The reaction mixture was stirred at 90° C. in pressure tube for 12 h. Major desired product mass by LCMS. The reaction mixture was concentrated to that residue was added water (50 ml), the product was extracted with ethylacetate (3*25 mL). The combined organic layer was dried over anhydrous sodium sulphate, filtered and concentrated to get (R)-2-(4-fluorobenzyl)-4-(4-(4-methoxyphenyl)piperidin-1-yl)isoxazolidin-3-one (0.15 g, 0.125 mmol, 28.6% yield) with LCMS purity 32% as brown gummy materail. The crude as such was taken for next step without further purification.

LCMS: Buffer:10 mM AmmoniumAcetate pH –5 adjusted with HCOOH, Mobile phase A:Buffer:ACN (95:5), Mobile phase B:Buffer:ACN (5:95), Method:% B: 0min-5%:1.1 min-95%:1.7 min-95% Column Name: Acquity BEH C18 (2.1×50 mm) 1.7 u Method:C:\MassLynx, Flow: 0.8 ml/min, RT-1.09 min, M(+1)–385.

To a stirred solution of 2-(4-fluorobenzyl)-4-(4-(4-methoxyphenyl)piperidin-1-yl)isoxazolidin-3-one (0.15 g, 0.125 mmol) in DCM (10 mL) was added BBR3 (2 mL, 21.16 mmol) at –78° C. temperature. The reaction mixture was stirred at –78° C. for 30 minutes. Major desired product mass by LCMS. The reaction mixture was quenched with 10% NaHCO3 50 ml and the product was extracted with DCM (3*25 mL). The combined organic layer was dried over anhydrous sodium sulphate, filtered and concentrated to get crude 0.16 g. The crude product was purified by HPLC to get 1 2-(4-fluorobenzyl)-4-(4-(4-hydroxyphenyl)piperidin-1-yl)isoxazolidin-3-one (22 mg, 0.059 mmol, 47.6%) as off white solid.

Chiral hplc of the example 1 shown two peaks and the racemic mixture was separated by Chiral HPLC/SFC to get P1 and P2.

Example 1 (Racemic Mixture)

LCMS 1: A: 95% Water: 5% Acetonitrile; 10 mM NH4OAC, B: 5% Water:95% Acetonitrile; 10 mM NH4OAC, Flow: 1.1 ml/min, Temp:50° C., Column: Ascentis Express C18 (50×2.1)mm, 2.7 μm, Time (min): 0 - - - 3, % B: 0 - - - 100, rt–1.495 min, M(+1)–371.

Example 1 (Racemic Mixture)

LCMS 2: A: 95% Water: 5% Acetonitrile; 0.1% TFA, B: 5% Water:95% Acetonitrile; 0.1% TFA, Flow: 1.1 ml/min, Temp:50° C., Column: Ascentis Express C18 (50×2.1)mm, 2.7 µm, Time (min): 0 - - - 3, % B: 0 - - - 100. RT-0.951 min, M(+1)–371.

Example 1 (Racemic Mixture)

1H NMR 400 MHz, MeOD: δ 1.90-1.98 (m, 2H), 2.07-2.11 (m, 2H), 2.76-2.80 (m, 1H), 3.11-3.17 (m, 1H), 3.42-3.51 (m, 2H), 3.90-3.92 (m, 1H), 4.59-4.73 (m, 3H), 4.80-4.86 (m, 2H), 6.76-6.78 (m, 2H), 7.08-7.15 (m, 4H), 7.40-7.44 (m, 2H).

Chiral Hplc: Injection Volume:10, Co-Solvent: 0.3% DEA in Methanol, Column: Chiralpak AD H (250×4.6)mm 5 u, Column Temperature: 22.9, Total Flow: 3, CO2 Flow Rate: 1.65, Co-Solvent Flow Rate: 1.35, Co-Solvent %: 45, Back Pressure: 101, Two diastereomer peaks were separated at RT1:3.03 min, 36.4% and RT2–8.21 min, 63.5%.
Preparative SFC Conditions:

Column/dimensions: Chiralpak AD-H (250×21)mm, 5 u, % CO2: 55%, % Co solvent: 45% (0.3% DEA in Methanol), Total Flow: 60.0 g/min, Back Pressure: 100 bar, Temperature: 25° C., UV: 220 nm, Solubility: Methanol 600.0 ml, Loadability/Inj: 6.0 mg/mL Total No of injections: 5, Total Time for purification 1.0 hrs.
For P-1 (Homochiral):

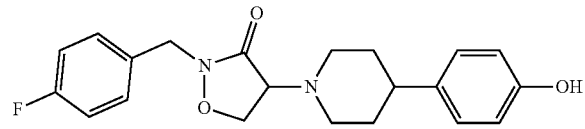

LCMS: Column-XBridge BEH C18 (50×4.6 mm-5 µm), Mphase A: 2% ACN-98% H20-10 mM NH4C00H Mphase B: 98% ACN-2% H20-10 mM NH4C00H, Flow=0.8 ML/MIN, Time:% B::0.0:10::7:100.0::15:100.0, RT-1.979 min, M(+1)–371.

1H NMR: 400 MHz, DMSO-d6: δ 1.49-1.56 (m, 2H), 1.68 (d, J=12.40 Hz, 2H), 2.27-2.35 (m, 2H), 2.72-2.81 (m, 2H), 3.08 (d, J=10.80 Hz, 1H), 3.81-3.85 (m, 1H), 4.20-4.24 (m, 1H), 4.35 (t, J=17.60 Hz, 1H), 4.65 (s, 2H), 6.66 (t, J=8.80 Hz, 2H), 7.00 (d, J=8.40 Hz, 2H), 7.16-7.20 (m, 2H), 7.32-7.36 (m, 2H), 9.18 (bs, 1H).

Chiral SFC: Injection Volume: 10, Co-Solvent: 0.3% DEA in Methanol, Column: Chiralpak AD H (250×4.6)mm 5 u, Column Temperature:23.9, Total Flow:3, CO2 Flow Rate: 1.65, Co-Solvent Flow Rate: 1:35, Co-Solvent %:45, Back Pressure: 100, RT-2.99 min.
For P-2 (Homochiral):

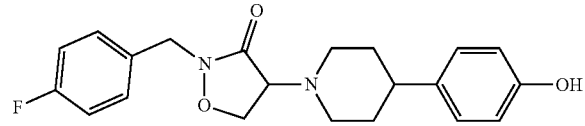

LCMS: A: 95% Water: 5% Acetonitrile; 10 mM NH4OAC, B: 5% Water:95%, Acetonitrile; 10 mM NH4OAC, Flow: 1.1 ml/min, Temp:50° C., Column: Ascentis Express C18 (50×2.1)mm, 2.7 µm, Time (min): 0 - - - 3, % B: 0 - - - 100 RT-1.450 min, M(+1)–371.

1H NMR: 400 MHz, MeOD: δ 1.68-1.81 (m, 4H), 2.43 (d, J=26.40 Hz, 2H), 2.84-2.92 (m, 2H), 3.20-3.26 (m, 1H), 3.89-3.92 (m, 1H), 4.32-4.36 (m, 1H), 4.42-4.47 (m, 1H), 4.73 (d, J=5.60 Hz, 2H), 6.71-6.73 (m, 2H), 7.04-7.12 (m, 4H), 7.37-7.41 (m, 2H), 9.18 (s, 1H).

Chiral SFC: Injection Volume: 10, Co-Solvent: 0.3% DEA in Methanol, Column: Chiralpak AD H (250×4.6)mm 5 u, Column Temperature:23.9, Total Flow:3, CO2 Flow Rate: 1.65, Co-Solvent Flow Rate: 1:35, Co-Solvent %:45, Back Pressure: 100, RT-7.88 min.

Example 2 (P1 & P2)

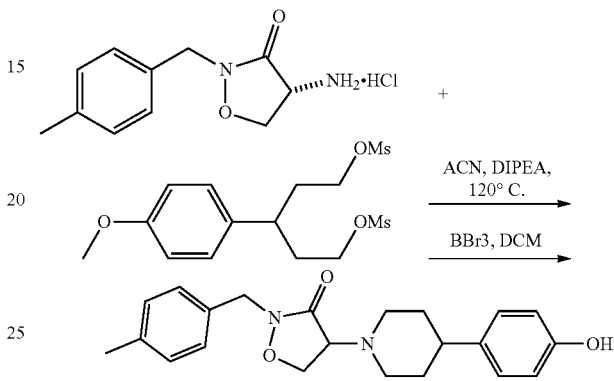

To a stirred solution of 3-(4-methoxyphenyl)pentane-1,5-diyl dimethanesulfonate (0.25 g, 0.682 mmol) in ACN (3 mL) was added (R)-4-amino-2-(4-methylbenzyl)isoxazolidin-3-one, HCl (0.166 g, 0.682 mmol) and DIPEA (0.357 mL, 2.047 mmol) at RT. The reaction mixture was stirred at 120° C. for 18 h in pressure tube. 14% expected product mass by LCMS. The reaction mixture was concentrated to remove ACN and was added water 50 ml, the product was extracted with ethylacetate (3*25 mL), the combined organic layer was dried over anhydrous sodium sulphate, filtered and concentrated to get crude 0.4 g. The crude product as such was taken for next step without further purification.

LCMS: Buffer:10 mM AmmoniumAcetate pH –5 adjusted with HCOOH, Mobile phase A:Buffer:ACN (95:5), Mobile phase B:Buffer:ACN (5:95), Method:% B: Omin-5%:1.1 min-95%:1.7 min-95% Column Name: Acquity BEH C18 (2.1×50 mm) 1.7 u Method:C:\MassLynx, Flow: 0.8 ml/min, RT-1.10 min, M(+1)–381. To a stirred solution of 4-(4-(4-methoxyphenyl)piperidin-1-yl)-2-(4-methylbenzyl)isoxazolidin-3-one (0.2 g, 0.526 mmol) in DCM (10 mL) was added BBR3 (2 mL, 21.16 mmol) at –78° C. temperature. The reaction mixture was stirred at –78° C. for 30 minutes. 19% desired product mass by LCMS. The reaction mixture was quenched with 10% NaHCO3 50 ml and the product was extracted with DCM 3*25 ml, the combined organic layer was dried over anhydrous sodium sulphate, filtered and concentrated to get crude 0.16 g. The crude product was purified by HPLC to get 2 4-(4-(4-hydroxyphenyl)piperidin-1-yl)-2-(4-methylbenzyl)isoxazolidin-3-one (42 mg, 0.115 mmol, 21.8%) as pale yellow solid. Chiral hplc of the example 2 shown two peaks and the racemic mixture was separated by Chiral HPLC/SFC to get P1 and P2

Example 2 (Racemic Mixture)

1H NMR 400 MHz, MeOD: δ 1.68-1.80 (m, 4H), 2.34 (s, 3H), 2.39-2.48 (m, 2H), 2.81-2.95 (m, 2H), 3.74-3.20 (m,

1H), 3.87-3.91 (m, 1H), 4.31-4.35 (m, 1H), 4.40-4.45 (m, 1H), 4.64-4.74 (m, 2H), 6.71-6.73 (m, 2H), 7.17-7.25 (m, 4H).
For P1 (Homochiral):

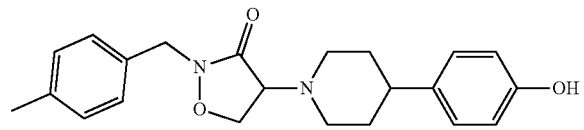

LCMS: A: 95% Water: 5% Acetonitrile; 10 mM NH4OAC, B: 5% Water:95% Acetonitrile; 10 mM NH4OAC, Flow: 1.1 ml/min, Temp:50° C., Column: Ascentis Express C18 (50×2.1)mm, 2.7 μm, Time (min): 0 - - - 3, % B: 0 - - - 100, RT-1.563 min, M(+1)–367.

1H NMR: 400 MHz, MeOD: δ 1.68-1.80 (m, 4H), 2.34 (s, 3H), 2.39-2.45 (m, 2H), 2.84-2.92 (m, 2H), 3.17 (t, J=26.00 Hz, 1H), 3.87-3.91 (m, 1H), 4.31-4.45 (m, 2H), 4.58-4.74 (m, 2H), 6.71-6.73 (m, 2H), 7.04-7.06 (m, 2H), 7.17-7.25 (m, 4H).

Chiral SFC: Injection Volume: 10, Co-Solvent: 0.3% DEA in Methanol, Column: Chiralpak AD H (250×4.6)mm 5 u, Column Temperature: 22.9, Total Flow: 4, CO2 Flow Rate: 2.4, Co-Solvent Flow Rate: 1.6, Co-Solvent %: 40, Back Pressure: 100, RT-3.11 min.
For P2 (Homochiral):

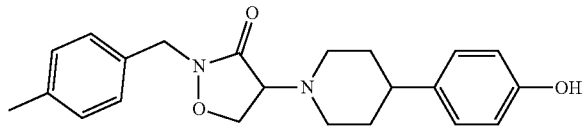 [SMILES: Cc1ccc(CN2OCC(N3CCC(c4ccc(O)cc4)CC3)C2=O)cc1]

LCMS: A: 95% Water: 5% Acetonitrile; 10 mM NH4OAC, B: 5% Water:95% Acetonitrile; 10 mM NH4OAC, Flow: 1.1 ml/min, Temp:50° C., Column: Ascentis Express C18 (50×2.1)mm, 2.7 μm, Time (min): 0 - - - 3, % B: 0 - - - 100, RT-1.566 min, M(+1)–367.

1H NMR: 400 MHz, MeOD: δ 1.68-1.80 (m, 4H), 2.34 (s, 3H), 2.40-2.45 (m, 2H), 2.84-2.92 (m, 2H), 3.18-3.20 (m, 1H), 3.87-3.91 (m, 1H), 4.31-4.45 (m, 2H), 4.64-4.86 (m, 2H), 6.71-6.73 (m, 2H), 7.04-7.06 (m, 2H), 7.17-7.25 (m, 4H).

Chiral SFC: Injection Volume: 10, Co-Solvent: 0.3% DEA in Methanol, Column: Chiralpak AD H (250×4.6)mm 5 u, Column Temperature: 22.9, Total Flow: 4, CO2 Flow Rate: 2.4, Co-Solvent Flow Rate: 1.6, Co-Solvent %: 40, Back Pressure: 99, RT-6.85 min.

Example 3 (Racemic Mixture)

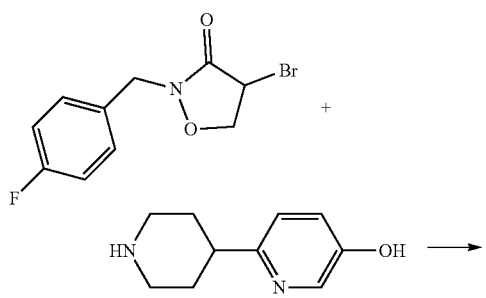

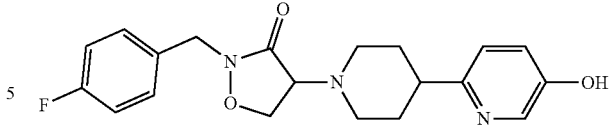

To a stirred solution of 4-bromo-2-(4-fluorobenzyl)isoxazolidin-3-one (0.031 g, 0.112 mmol) in DMF (2 mL) was added DIPEA (0.059 mL, 0.337 mmol) and 6-(piperidin-4-yl)pyridin-3-ol (0.02 g, 0.112 mmol) at RT. The reaction mixture was stirred at RT for 18 h. 32% Desired product mass by LCMS. The reaction mixture was purified by HPLC to get 2-(4-fluorobenzyl)-4-(4-(5-hydroxypyridin-2-yl)piperidin-1-yl)isoxazolidin-3-one (2.2 mg, 5.86 μma 5.23% yield) as pale yellow solid.

LCMS (Ammonium acetate method): A: 95% Water: 5% Acetonitrile; 10 mM NH4OAC, B: 5% Water:95% Acetonitrile; 10 mM NH4OAC, Flow: 1.1 ml/min, Temp:50° C., Column: Ascentis Express C18 (50×2.1)mm, 2.7 μm, Time (min): 0 - - - 3, % B: 0 - - - 100, RT-1.159 min, M(+1)–372.

LCMS (TFA method): A: 95% Water: 5% Acetonitrile; 0.1% TFA, B: 5% Water:95% Acetonitrile; 0.1% TFA, Flow: 1.1 ml/min, Temp:50° C., Column: Ascentis Express C18 (50×2.1)mm, 2.7 μm, Time (min): 0 - - - 3, % B: 0 - - - 100, RT-0.675 min, M(+1)–372.

1H NMR: 400 MHz, DMSO-d6: δ 1.61-1.65 (m, 2H), 1.74-1.77 (m, 2H), 2.30-2.33 (m, 1H), 2.51-2.55 (m, 1H), 2.73-2.74 (m, 1H), 2.79-2.82 (m, 1H), 3.16-3.18 (m, 1H), 3.81-3.85 (m, 1H), 4.20-4.24 (m, 1H), 4.35-4.37 (m, 1H), 4.65 (s, 2H), 7.07-7.07 (m, 2H), 7.16-7.20 (m, 2H), 7.32-7.36 (m, 2H), 8.03 (d, J=3.60 Hz, 1H), 9.64 (s, 1H).

Example 4 (Racemic Mixture)

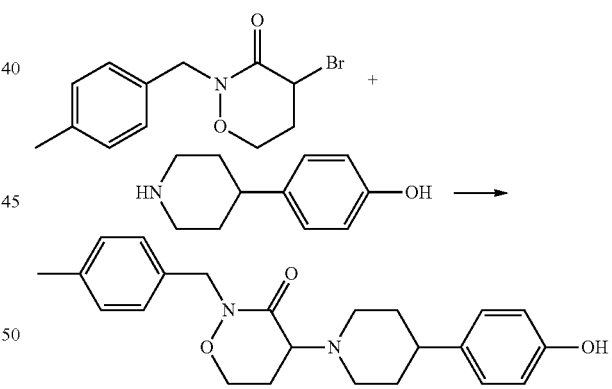

To a solution of 4-(piperidin-4-yl)phenol, HCl (0.026 g, 0.123 mmol) in Acetonitrile (3 mL) was added DIPEA (0.065 mL, 0.370 mmol) followed by 4-bromo-2-(4-methylbenzyl)-1,2-oxazinan-3-one (0.035 g, 0.123 mmol). The mixture was then stirred at 80° C. for 16 h. The mixture was allowed to cool to RT and then concentrated. The crude material was purified via preparative LC/MS with the following conditions: Waters Xbridge C18,19×150 mm, 5 μm; Guard Column:Waters XBridge C18,19×10 mm, 5 μm; Mobile Phase A:5:95 Acetonitrile:water with 0.1% TFA; Mobile Phase B: 95:5 Acetonitrile:water with 0.1% TFA; Gradient:10-50% B over 25 minutes, followed by a 10 minute hold at 50% B and 5 minute hold at 100% B; Flow:15 ml/min. Fractions containing the desired product were combined and dried using a Genevac centrifugal evaporator to obtained 4 4-(4-(4-hydroxyphenyl)piperidin-1-yl)-2-(4-methylbenzyl)-1,2-oxazinan-3-one (6 mg, 0.015 mmol, 12.55% yield) as pale yellow solid. The racemic mixture was separated by Chiral HPLC/SFC to get P1 and P2.

LCMS: A: 95% Water: 5% Acetonitrile; 10 mM NH4OAC, B: 5% Water:95% Acetonitrile; 10 mM NH4OAC, Flow: 1.1 ml/min, Temp:50° C., Column: Ascentis Express C18 (50×2.1)mm, 2.7 μm, Time (min): 0 - - - 3, % B: 0 - - - 100, RT:1.689 min, (M+1)=381.

$^1$H NMR: 400 MHz, DMSO-d6: δ 1.93-1.99 (m, 4H), 2.21 (bs, 1H), 2.30 (s, 3H), 2.73-2.75 (m, 1H), 3.22-3.25 (m, 3H), 3.49-3.59 (m, 2H), 4.03 (bs, 1H), 4.24 (bs, 1H), 4.60 (bs, 1H), 4.72 (d, J=15.20 Hz, 1H), 4.81 (d, J=15.60 Hz, 1H), 6.73 (d, J=8.00 Hz, 2H), 7.04 (d, J=8.40 Hz, 2H), 7.17-7.23 (m, 4H), 9.26 (s, 1H).

Example 5 (P1 & P2)

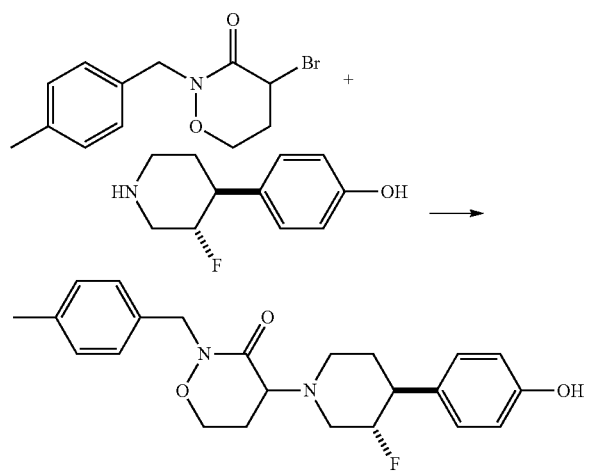

To a solution of 4-((3S,4S)-3-fluoropiperidin-4-yl)phenol, HCl (0.05 g, 0.216 mmol) and DIPEA (0.113 mL, 0.647 mmol) in Acetonitrile (3 mL) was added 4-bromo-2-(4-methylbenzyl)-1,2-oxazinan-3-one (0.092 g, 0.324 mmol) and heated to 80° C. for overnight. The completion of the reaction was monitored by LCMS. Reaction mixture was concentrated under reduced pressure. The crude was purified by SCP obtained example 6 4-((3S,4S)-3-fluoro-4-(4-hydroxyphenyl)piperidin-1-yl)-2-(4-methylbenzyl)-1,2-oxazinan-3-one (1.4 mg, 3.44 μmol, 1.596% yield) and remaining compound was separated by SFC obtained P1 4-((3S,4S)-3-fluoro-4-(4-hydroxyphenyl)piperidin-1-yl)-2-(4-methylbenzyl)-1,2-oxazinan-3-one (5.5 mg, 0.013 mmol, 6.08% yield) and P2 4-((3S,4S)-3-fluoro-4-(4-hydroxyphenyl)piperidin-1-yl)-2-(4-methylbenzyl)-1,2-oxazinan-3-one (2.7 mg, 6.57 μmol, 3.05% yield). The diasteromeric mixture was separated by Chiral HPLC/SFC to get P1 and P2.

SFC Purification Method:
Analytical SFC Conditions: Column/dimensions: Chiralpak OJ-H(250×4.6)mm, 5 u, % CO2: 70%, % Co solvent: 30%(0.25% DEA in Methanol), Total Flow: 3.0 g/min, Back Pressure: 100 bar, Temperature: 25° C., UV: 220.

Preparative SFC Conditions: Column/dimensions: Chiralpak OJ-H(250×21)mm, 5 u, % CO2: 70%, % Co solvent: 30%(0.25% DEA in Methanol), Total Flow: 60.0 g/min, Back Pressure: 100 bar, Temperature: 25° C., UV: 220, Peak number: Retention Time::Peak 1:6.80::Peak 2:7.70

Solubility: Methanol 5 ml, Loadability/Inj: 1.80 mg/mL, Total No of injections:7, Total Time for purification 0.3 hrs, Instrument details: Make/Model: Thar SFC-80.

For P1 (Homochiral):

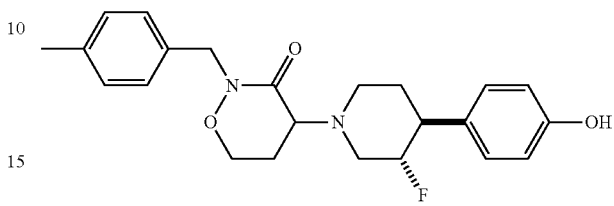

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, Time:% B::0.0:0.0::1.7:100.0::3.0:100.0::3.2:0.0, RT-2.699 min, (M+1)–399.

Chiral purity: Injection Volume: 10, Co-Solvent: 0.3% DEA in Methanol, Column: Chiralcel OJ-H(4.6×250)mm, 5 u, Column Temperature: 23.5, Total Flow: 3, CO2 Flow Rate: 2.1, Co-Solvent Flow Rate: 0.9, Co-Solvent %: 30, Back Pressure: 100, RT-6.66 min.

H-NMR: 400 MHz, MeOD: δ 1.80-1.83 (m, 2H), 2.08-2.11 (m, 1H), 2.32 (s, 3H), 2.33-2.38 (m, 1H), 2.57-2.70 (m, 3H), 2.90-2.93 (m, 1H), 3.35-3.36 (m, 1H), 3.73 (t, J=10.00 Hz, 1H), 3.97-4.07 (m, 2H), 4.53-4.70 (m, 2H), 4.77 (d, J=14.80 Hz, 1H), 6.74 (dd, J=8.80, Hz, 2H), 7.09 (dd, J=8.80, Hz, 2H), 7.15 (d, J=8.00 Hz, 2H), 7.23 (d, J=8.00 Hz, 2H).

For P2 (Homochiral):

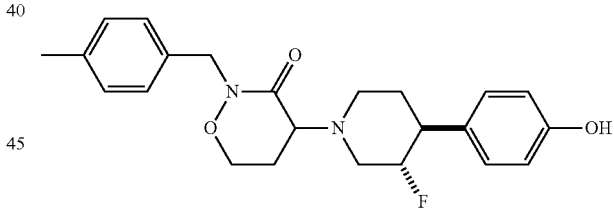

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, Time:% B::0.0:0.0::1.7:100.0::3.0:100.0::3.2:0.0, RT-2.715 min, (M+1)–399.

Chiral Purity: Injection Volume: 10, Co-Solvent: 0.3% DEA in Methanol, Column: Chiralcel OJ-H(4.6×250)mm, 5 u, Column Temperature: 23.5, Total Flow: 3, CO2 Flow Rate: 2.1, Co-Solvent Flow Rate: 0.9, Co-Solvent %: 30, Back Pressure: 100, RT-7.77 min.

H-NMR: 400 MHz, MeOD: δ 1.78-1.82 (m, 2H), 2.08-2.12 (m, 1H), 2.32 (s, 3H), 2.33-2.37 (m, 1H), 2.58-2.71 (m, 3H), 2.91-2.94 (m, 1H), 3.33-3.35 (m, 1H), 3.70-3.75 (m, 1H), 3.97-4.07 (m, 2H), 3.52-3.64 (m, 1H), 4.67 (d, J=14.80 Hz, 1H), 4.76 (d, J=14.80 Hz, 1H), 6.74 (dd, J=8.40, Hz, 2H), 7.09 (dd, J=8.40, Hz, 2H), 7.15 (d, J=8.00 Hz, 2H), 7.22 (d, J=8.00 Hz, 2H).

Example 6 (P1 and P2)

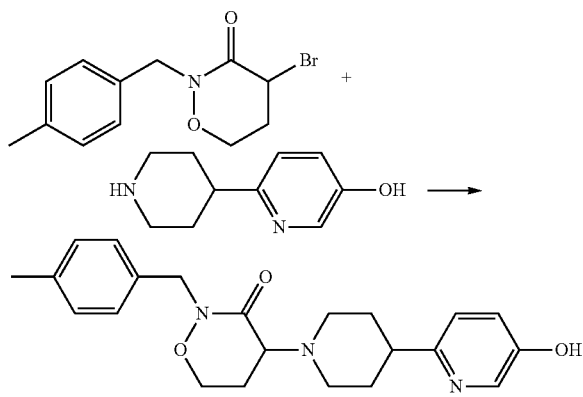

To a solution of 6-(piperidin-4-yl)pyridin-3-ol, HCl (0.05 g, 0.233 mmol) in Acetonitrile (3 mL) was added DIPEA (0.122 mL, 0.699 mmol) followed by 4-bromo-2-(4-methylbenzyl)-1,2-oxazinan-3-one (0.132 g, 0.466 mmol). The mixture was then stirred at 80° C. for 16 h. The mixture was allowed to cool to RT and then concentrated to get crude 0.2 g. The crude was purified by SCP. The crude material was purified via preparative LC/MS with the following conditions: Waters Xbridge C18,19×150 mm, 5 μm; Guard Column:Waters XBridge C18,19×10 mm, 5 μm; Mobile Phase A:5:95 Acetonitrile:water with 10 mM NH4OAc; Mobile Phase B: 95:5 Acetonitrile:water with 10 mM NH4OAc; Gradient:10-40% B over 25 minutes, followed by a 10 minute hold at 40% B and 5 minute hold at 100% B; Flow:15 ml/min. Fractions containing the desired product were combined and dried using a Genevac centrifugal evaporator to obtained example 7 4-(4-(5-hydroxypyridin-2-yl)piperidin-1-yl)-2-(4-methylbenzyl)-1,2-oxazinan-3-one (1.4 mg, 3.67 μmol, 1.576% yield). The racemic mixture was separated by Chiral HPLC/SFC to get P1 and P2.

The racemic compound was separated by SFC obtained P1 4-(4-(5-hydroxypyridin-2-yl)piperidin-1-yl)-2-(4-methylbenzyl)-1,2-oxazinan-3-one (8.4 mg, 0.022 mmol, 9.36% yield) and P2 4-(4-(5-hydroxypyridin-2-yl)piperidin-1-yl)-2-(4-methylbenzyl)-1,2-oxazinan-3-one (8 mg, 0.021 mmol, 8.91% yield).

SFC Condition:

Analytical SFC Conditions: Column/dimensions: Chiralcel OD-H(250×4.6)mm, 5 u, % CO2: 75%, % Co solvent: 25%(0.25% DEA in Methanol), Total Flow: 3.0 g/min, Back Pressure: 100 bar, Temperature: 25° C., UV: 219.

Preparative SFC Conditions: Column/dimensions: Chiralcel OD-H(250×21)mm, 5 u % CO2: 75%, % Co solvent: 25%(0.25% DEA in Methanol), Total Flow: 60.0 g/min, Back Pressure: 100 bar, Temperature: 25° C., UV: 219: Peak number: Retention Time::Peak 1:3.60::Peak 2:4.50, Solubility: Methanol in 10.0 ml, Loadability/Inj: 5.0 mg/mL, Total No of injections:10, Total Time for purification 1.0 hr, Instrument details: Make/Model: Thar SFC-80.

For P1 (Homochiral):

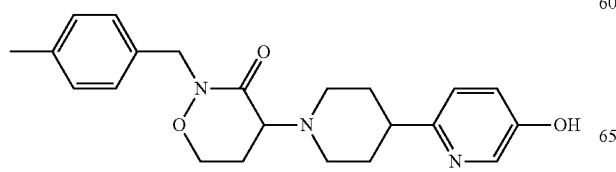

LCMS: Column-Ascentis Express C8 (50×2.1 mm-2.7 μm), Mphase A: 2% ACN-98% H20-10 mM NH4C00H, Mphase B: 98% ACN-2% H20-10 mM NH4C00H, Flow=1 ML/MIN, Time:% B::0.0:0.0::1.5:100.0::3.2:100.0, RT-1.782 min, (M+1)–382.

Chiral SFC: Injection Volume: 10, Co-Solvent: 0.3% DEA in Methanol, Column: Chiralcel OD-H(4.6×250)mm, 5 u, Column Temperature: 23.5, Total Flow: 3, CO2 Flow Rate: 2.25, Co-Solvent Flow Rate: 0.75, Co-Solvent %: 25, Back Pressure: 104, RT-4.04 min.

H-NMR: 400 MHz, MeOD: δ 1.81-1.91 (m, 4H), 2.10-2.14 (m, 1H), 2.34 (s, 3H), 1.36-2.41 (m, 1H), 2.62-2.70 (m, 2H), 2.80 (td, J=22.40, Hz, 1H), 3.09 (s, 2H), 3.65-3.70 (m, 1H), 3.99-4.07 (m, 2H), 4.69 (d, J=14.80 Hz, 1H), 4.78 (d, J=14.80 Hz, 1H), 7.16-7.18 (m, 4H), 7.25 (d, J=8.00 Hz, 2H), 7.98-7.99 (m, 1H).

For P2 (Homochiral):

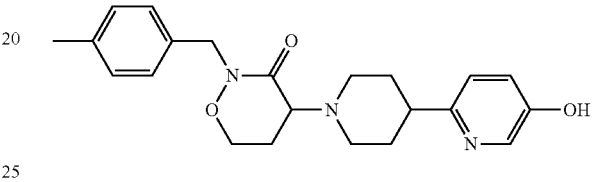

LCMS: Column-Ascentis Express C8 (50×2.1 mm-2.7 μm), Mphase A: 2% ACN-98% H20-10 mM NH4C00H, Mphase B: 98% ACN-2% H20-10 mM NH4C00H, Flow=1 ML/MIN, Time:% B::0.0:0.0::1.5:100.0::3.2:100.0::RT-1.798 min, (M+1)–382.

Chiral SFC: Injection Volume: 10, Co-Solvent: 0.3% DEA in Methanol, Column: Chiralcel OD-H(4.6×250)mm, 5 u, Column Temperature: 23.5, Total Flow: 3, CO2 Flow Rate: 2.25, Co-Solvent Flow Rate: 0.75, Co-Solvent %: 25, Back Pressure: 98, RT-4.43 min.

H-NMR: 400 MHz, MeOD: δ 1.81-1.91 (m, 4H), 2.10-2.14 (m, 1H), 2.34 (s, 3H), 1.36-2.41 (m, 1H), 2.62-2.70 (m, 2H), 2.80 (td, J=22.40, Hz, 1H), 3.09 (s, 2H), 3.65-3.70 (m, 1H), 3.99-4.07 (m, 2H), 4.69 (d, J=14.80 Hz, 1H), 4.78 (d, J=14.80 Hz, 1H), 7.16-7.20 (m, 4H), 7.25 (d, J=8.00 Hz, 2H), 8.00-8.01 (m, 1H).

Example 7 (P1 & P2)

(3R,4R)-3-fluoro-4-(4-hydroxyphenyl)piperidin-1-yl)-2-(4-methylbenzyl)-1,2-oxazinan-3-one

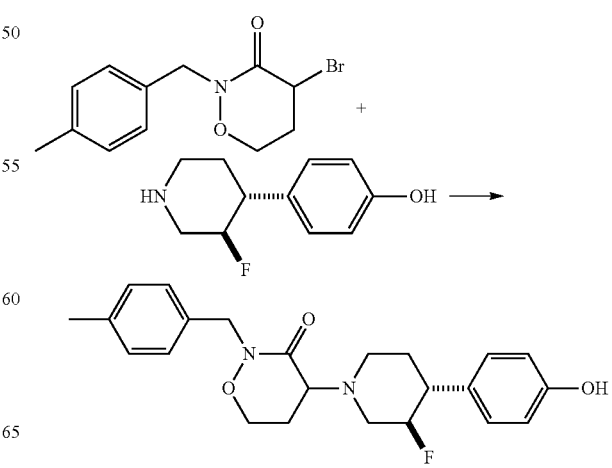

To a solution of 4-((3R,4R)-3-fluoropiperidin-4-yl)phenol, HCl (0.05 g, 0.216 mmol) in Acetonitrile (3 mL) was added DIPEA (0.113 mL, 0.647 mmol) followed by 4-bromo-2-(4-methylbenzyl)-1,2-oxazinan-3-one (0.123 g, 0.432 mmol). The mixture was then stirred at 80° C. for 16 h. The mixture was allowed to cool to RT and then concentrated. The residue was purified by SCP. The crude material was purified via preparative LC/MS with the following conditions: Waters Xbridge C18,19×150 mm, 5 μm; Guard Column:Waters XBridge C18,19×10 mm, 5 μm; Mobile Phase A:5:95 Acetonitrile:water with 10 mM NH4OAc; Mobile Phase B: 95:5 Acetonitrile:water with 10 mM NH4OAc; Gradient:10-40% B over 25 minutes, followed by a 10 minute hold at 40% B and 5 minute hold at 100% B; Flow:15 ml/min. Fractions containing the desired product were combined and dried using a Genevac centrifugal evaporator obtained example 8 4-((3R,4R)-3-fluoro-4-(4-hydroxyphenyl)piperidin-1-yl)-2-(4-methylbenzyl)-1,2-oxazinan-3-one (1.4 mg, 3.51 μmol, 1.628% yield). The Diasteromeric mixture was separated by Chiral HPLC/SFC to get P1 and P2.

The compound was separated by SFC obtained P1 4-((3R,4R)-3-fluoro-4-(4-hydroxyphenyl)piperidin-1-yl)-2-(4-methylbenzyl)-1,2-oxazinan-3-one (14.1 mg, 0.035 mmol, 16.23% yield) and P2 4-((3R,4R)-3-fluoro-4-(4-hydroxyphenyl)piperidin-1-yl)-2-(4-methylbenzyl)-1,2-oxazinan-3-one (12.9 mg, 0.032 mmol, 14.85% yield).
SFC Condition:

Analytical SFC Conditions: Column/dimensions: Chiralcel OD-H(250×4.6)mm, 5 u, % CO2: 75%, % Co solvent: 25%(0.25% DEA in Methanol), Total Flow: 3.0 g/min, Back Pressure: 100 bar, Temperature: 25° C. UV: 219.

Preparative SFC Conditions: Column/dimensions: Chiralcel OD-H(250×21)mm, 5 u, % CO2: 75%, % Co solvent: 25%(0.25% DEA in Methanol), Total Flow: 60.0 g/min, Back Pressure: 100 bar, Temperature: 25° C., UV: 219, Peak number: Retention Time::Peak 1:6.50::Peak 2:8.50, Solubility: Methanol in 10.0 ml, Loadability/Inj: 5.0 mg/mL, Total No of injections:10, Total Time for purification 1.0 hr, Instrument details: Make/Model: Thar SFC-80.
For P1 (Homochiral):

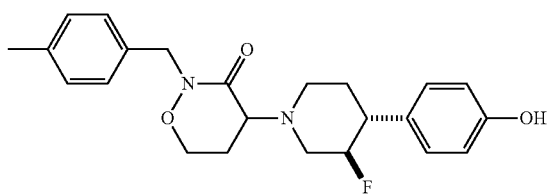 [SMILES: Cc1ccc(CN2OCCC(N3CC[C@H](c4ccc(O)cc4)[C@@H](F)C3)C2=O)cc1]

LCMS: Column-Ascentis Express C8 (50×2.1 mm-2.7 μm), Mphase A: 2% ACN-98% H20-10 mM NH4C00H Mphase B: 98% ACN-2% H20-10 mM NH4C00H, Flow=1 ML/MIN, Time:% B::0.0:0.0::1.5:100.0::3.2:100.0, RT-1.96 min, (M+1)− 399.

H-NMR: 400 MHz, MeOD: δ 1.80-1.85 (m, 2H), 2.09-2.15 (m, 1H), 2.35 (s, 3H), 2.36-2.41 (m, 1H), 2.55-2.67 (m, 2H), 2.72-2.79 (m, 1H), 2.95-2.98 (m, 1H), 3.35-3.37 (m, 1H), 3.73-3.77 (m, 1H), 3.99-4.02 (m, 1H), 4.05-4.10 (m, 1H), 4.53-4.67 (m, 1H), 4.70 (d, J=14.80 Hz, 1H), 4.79 (d, J=14.80 Hz, 1H), 6.76 (dt, J=14.40, Hz, 2H), 7.12 (dt, J=14.00, Hz, 2H), 7.17 (d, J=8.00 Hz, 2H), 7.25 (d, J=8.00 Hz, 2H).

Chiral SFC: Injection Volume: 10, Co-Solvent: 0.3% DEA in Methanol, Column: Chiralcel OD-H(4.6×250)mm, 5 u, Column Temperature: 23.6, Total Flow: 3, CO2 Flow Rate: 2.25,
Co-Solvent Flow Rate: 0.75, Co-Solvent %: 25, Back Pressure: 103, RT-5.88 min.
For P2 (Homochiral):

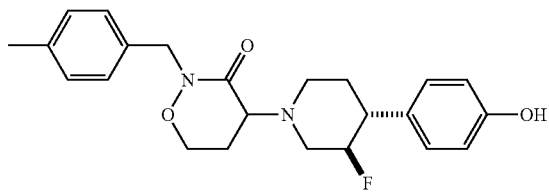 [SMILES: Cc1ccc(CN2OCCC(N3CC[C@H](c4ccc(O)cc4)[C@@H](F)C3)C2=O)cc1]

LCMS: Column-Ascentis Express C8 (50×2.1 mm-2.7 μm), Mphase A: 2% ACN-98% H20-10 mM NH4C00H Mphase B: 98% ACN-2% H20-10 mM NH4C00H, Flow=1 ML/MIN, Time:% B::0.0:0.0::1.5:100.0::3.2:100.0, RT-1.965 min, (M+1):399.

H-NMR: 400 MHz, MeOD: δ 1.81-1.86 (m, 2H), 2.07-2.13 (m, 1H), 2.35 (s, 3H), 2.36-2.41 (m, 1H), 2.54-2.74 (m, 3H), 2.93-2.96 (m, 1H), 3.36-3.37 (m, 1H), 3.74-3.78 (m, 1H), 3.99-4.03 (m, 1H), 4.05-4.10 (m, 1H), 4.54-4.67 (m, 1H), 4.70 (d, J=14.80 Hz, 1H), 4.79 (d, J=15.20 Hz, 1H), 6.76 (dt, J=11.20, Hz, 2H), 7.11 (dt, J=11.20, Hz, 2H), 7.18 (d, J=8.00 Hz, 2H), 7.25 (d, J=8.00 Hz, 2H).

Chiral SFC: Injection Volume: 10, Co-Solvent: 0.3% DEA in Methanol, Column: Chiralcel OD-H(4.6×250)mm, 5 u, Column Temperature: 23.6, Total Flow: 3, CO2 Flow Rate: 2.25,
Co-Solvent Flow Rate: 0.75, Co-Solvent %: 25, Back Pressure: 105, RT-6.77 min.

Example 8 (P1 & P2)

4-(4-(5-hydroxypyridin-2-yl)piperazin-1-yl)-2-(4-methylbenzyl)-1,2-oxazinan-3-one

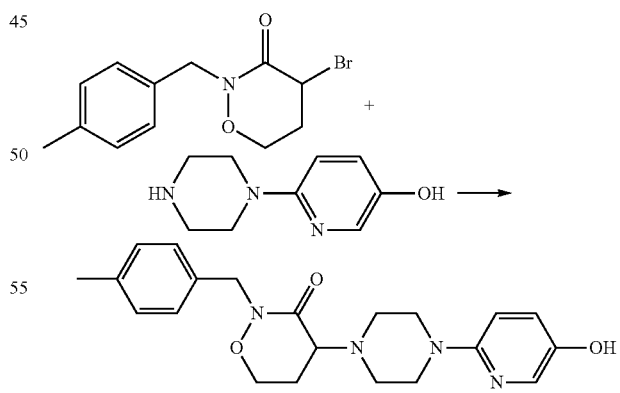

To a solution of 6-(piperazin-1-yl)pyridin-3-ol, HCl (0.05 g, 0.232 mmol) in Acetonitrile (3 mL) was added DIPEA (0.243 mL, 1.394 mmol) followed by 4-bromo-2-(4-methylbenzyl)-1,2-oxazinan-3-one (0.132 g, 0.465 mmol). The mixture was then stirred at 80° C. for 16 h. The mixture was allowed to cool to RT and then concentrated. The residue was purified by SCP. The crude material was purified via preparative LC/MS with the following conditions: Waters Xbridge C18,19×150 mm, 5 μm; Guard Column:Waters XBridge C18,19×10 mm, 5 μm; Mobile Phase A:5:95 Acetonitrile:water with 10 mM NH4OAc; Mobile Phase B: 95:5 Acetonitrile:water with 10 mM NH4OAc; Gradient: 10-40% B over 25 minutes, followed by a 10 minute hold at 40% B and 5 minute hold at 100% B; Flow:15 ml/min. Fractions containing the desired product were combined and dried using a Genevac centrifugal evaporator obtained example 8 4-(4-(5-hydroxypyridin-2-yl)piperazin-1-yl)-2-(4-methylbenzyl)-1,2-oxazinan-3-one. The racemic mixture 8 was separated by Chiral HPLC/SFC to get P1 and P2.

The compound 8 was separated obtained P1 4-(4-(5-hydroxypyridin-2-yl)piperazin-1-yl)-2-(4-methylbenzyl)-1,2-oxazinan-3-one (5.7 mg, 0.014 mmol, 3.08% yield) and P2 4-(4-(5-hydroxypyridin-2-yl)piperazin-1-yl)-2-(4-methylbenzyl)-1,2-oxazinan-3-one (4.9 mg, 0.012 mmol, 2.68% yield).

SFC Purification Condition:

Analytical SFC Conditions: Column/dimensions: Chiralcel OD-H(250×4.6)mm, 5 u, % CO2: 60%, % Co solvent: 40%(0.25% DEA in Methanol), Total Flow: 4.0 g/min, Back Pressure: 100 bar, Temperature: 25° C. UV: 246.

Preparative SFC Conditions: Column/dimensions: Chiralcel OD-H(250×21)mm, 5 u, % CO2: 60%, % Co solvent: 40%(0.25% DEA in Methanol), Total Flow: 60.0 g/min, Back Pressure: 100 bar, Temperature: 25° C., UV: 246, Peak number: Retention Time::Peak 1:4.00::Peak 2:5.00, Solubility: Methanol in 5.0 ml, Loadability/Inj: 4.0 mg/mL, Total No of injections:5, Total Time for purification 1.0 hr, Instrument details: Make/Model: Thar SFC-80.

For P1 (Homochiral):

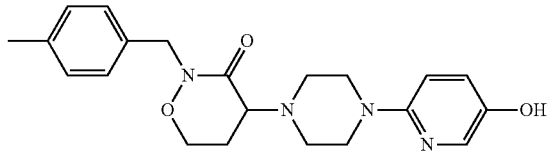

LCMS: Column-Ascentis Express C18 (50×2.1 mm-2.7 μm), Mphase A: 10 mM Ammonium Acetate in water, Mphase B: CAN, Flow=1 ML/MIN, Time: % A: % B::0.0: 100.0:0.0::1.7:0.0:100.0::3.2:0.0:100.0, RT-2.007 min; (M+1):383.

H-NMR: 400 MHz, MeOD: δ 2.04-2.10 (m, 1H), 2.32 (s, 3H), 2.34-2.41 (m, 1H), 2.84-2.89 (m, 2H), 2.91-2.96 (m, 2H), 3.37 (t, J=10.00 Hz, 4H), 3.64-3.69 (m, 1H), 3.95-3.99 (m, 1H), 4.02-4.06 (m, 1H), 4.66 (d, J=15.20 Hz, 1H), 4.77 (d, J=15.20 Hz, 1H), 6.76 (d, J=9.20 Hz, 1H), 7.12-7.16 (m, 3H), 7.20-7.23 (m, 2H), 7.73 (d, J=3.20 Hz, 1H).

Chiral SFC: Injection Volume: 10, Co-Solvent: 0.3% DEA in Methanol, Column: Chiralcel OD-H(4.6×250)mm, 5 u, Column Temperature: 24.5, Total Flow: 4, CO2 Flow Rate: 2.4, Co-Solvent Flow Rate: 1.6, Co-Solvent %: 40, Back Pressure: 74, RT-2.81 min.

For P2 (Homochiral):

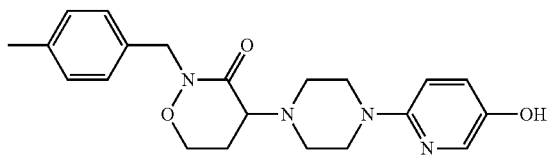

LCMS: Column-Ascentis Express C18 (50×2.1 mm-2.7 μm), Mphase A: 10 mM Ammonium Acetate in water, Mphase B: CAN, Flow=1 ML/MIN, Time: % A: % B::0.0: 100.0:0.0::1.7:0.0:100.0::3.2:0.0:100.0, RT-2.005 min; (M+1):383.

1H-NMR: 400 MHz, MeOD: δ 2.04-2.10 (m, 1H), 2.32 (s, 3H), 2.34-2.41 (m, 1H), 2.84-2.89 (m, 2H), 2.91-2.96 (m, 2H), 3.37 (t, J=10.00 Hz, 4H), 3.64-3.69 (m, 1H), 3.95-3.99 (m, 1H), 4.02-4.06 (m, 1H), 4.66 (d, J=15.20 Hz, 1H), 4.77 (d, J=15.20 Hz, 1H), 6.76 (d, J=9.20 Hz, 1H), 7.12-7.16 (m, 3H), 7.20-7.23 (m, 2H), 7.73 (d, J=3.20 Hz, 1H).

Chiral SFC: Injection Volume: 10, Co-Solvent: 0.3% DEA in Methanol, Column: Chiralcel OD-H(4.6×250)mm, 5 u, Column Temperature: 24.5, Total Flow: 4, CO2 Flow Rate: 2.4, Co-Solvent Flow Rate: 1.6, Co-Solvent %: 40, Back Pressure: 74, RT-3.68 min.

Example 9 (P1 & P2)

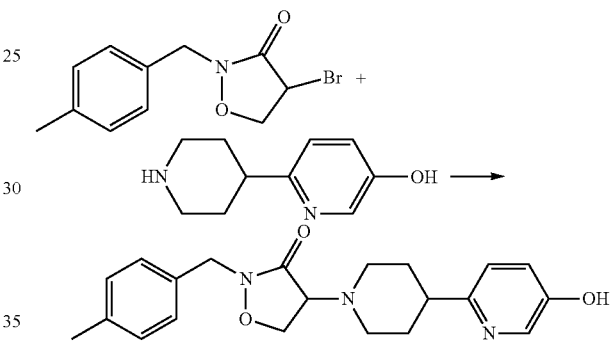

4-bromo-2-(4-methylbenzyl)isoxazolidin-3-one (0.094 g, 0.349 mmol) in ACN (5 mL) was added DIPEA (0.122 mL, 0.699 mmol) and 6-(piperidin-4-yl)pyridin-3-ol, HCl (0.05 g, 0.233 mmol) at RT. The reaction mixture was stirred at 60° C. for 18 h. 13% Desired product mass by LCMS. The reaction mixture was concentrated and was submitted to SCP. The compound was purified by SCP to get racemic mixture 10, 4-(4-(5-hydroxypyridin-2-yl)piperidin-1-yl)-2-(4-methylbenzyl)isoxazolidin-3-one (13 mg, 0.035 mmol, 14.89% yield) and was racemic mixture was separated by Chiral SFC to get P1 4-(4-(5-hydroxypyridin-2-yl)piperidin-1-yl)-2-(4-methylbenzyl)isoxazolidin-3-one (1.6 mg, 4.18 μmol, 1.795% yield) and P2 4-(4-(5-hydroxypyridin-2-yl)piperidin-1-yl)-2-(4-methylbenzyl)isoxazolidin-3-one (2.7 mg, 6.83 μmol, 2.93% yield).

SFC Purification Method

Analytical SFC Conditions: Column/dimensions: Lux Amylose-2(250×4.6)mm, 5 u, % CO2: 60%, % Co solvent: 40%(0.25% DEA in Methanol), Total Flow: 3.0 g/min, Back Pressure: 100 bar, Temperature: 25° C., UV: 220.

Preparative SFC Conditions: Column/dimensions: Lux Amylose-2(250×21.5)mm, 5 u, % CO2: 60%, % Co solvent: 40%(0.25% DEA in Methanol), Total Flow: 60.0 g/min, Back Pressure: 100 bar, Temperature: 25° C., UV: 220, Peak number: Retention Time::Peak 1:3.50::Peak 2 5.10::Solubility: Methanol in 10.0 ml, Loadability/Inj: 3.0 mg/mL, Total No of injections:09, Total Time for purification 1.00 hr, Instrument details: Make/Model: Thar SFC-80.

For P1 (Homochiral):

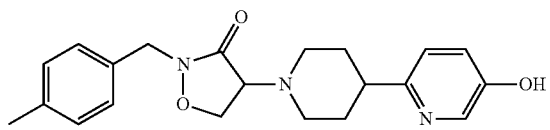 [SMILES: Cc1ccc(CN2OCC(N3CCC(c4ccc(O)cn4)CC3)C2=O)cc1]

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, Time: % B::0.0:0.0::1.7:100.0::3.0:100.0::3.2:0.0, RT-2.019 min, M(+1)–368.

Chiral purity: Injection Volume: 10, Co-Solvent: 0.3% DEA in Methanol, Column: Lux amylose-2(250×4.6)mm 5 u, Column Temperature: 22.1, Total Flow:3, CO2 Flow Rate: 2.1, Co-Solvent Flow Rate: 0.9, Co-Solvent %: 30, Back Pressure: 103, RT-4.46 min.

1H NMR: 400 MHz, MeOD: δ 1.74-1.91 (m, 5H), 2.31 (s, 3H), 2.43 (t, J=11.20 Hz, 1H), 2.62 (t, J=16.00 Hz, 1H), 2.86-2.95 (m, 2H), 3.18-3.22 (m, 1H), 3.88-3.91 (m, 1H), 4.31-4.35 (m, 1H), 4.40-4.45 (m, 1H), 4.64-4.74 (m, 2H), 7.15-7.25 (m, 6H), 7.98-7.99 (m, 1H).

For P2 (Homochiral):

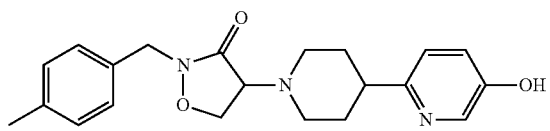 [SMILES: Cc1ccc(CN2OCC(N3CCC(c4ccc(O)cn4)CC3)C2=O)cc1]

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, Time:% B::0.0:0.0::1.7:100.0::3.0:100.0, 3.2:0.0, RT-2.021 min, M(+1)–368.

Chiral purity: Injection Volume: 10, Co-Solvent: 0.3% DEA in Methanol, Column: Lux amylose-2(250×4.6)mm 5 u, Column Temperature: 22.1, Total Flow: 3, CO2 Flow Rate: 2.1, Co-Solvent Flow Rate: 0.9, Co-Solvent %: 30, Back Pressure: 102, RT-5.67 min.

1H NMR: 400 MHz, MeOD: δ 1.74-1.91 (m, 4H), 2.31 (s, 3H), 2.43 (t, J=11.20 Hz, 1H), 2.62 (t, J=16.00 Hz, 1H), 2.86-2.95 (m, 2H), 3.18-3.22 (m, 1H), 3.88-3.91 (m, 1H), 4.31-4.35 (m, 1H), 4.40-4.45 (m, 1H), 4.64-4.74 (m, 2H), 7.15-7.25 (m, 6H), 7.98-7.99 (m, 1H).

Example 10 (P1 and P2)

4-(4-(5-hydroxypyridin-2-yl)piperazin-1-yl)-2-(4-methylbenzyl)isoxazolidin-3-one

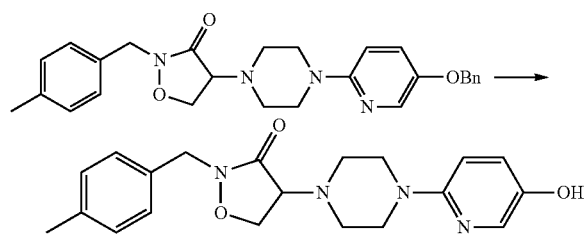

To a solution 4-(4-(5-(benzyloxy)pyridin-2-yl)piperazin-1-yl)-2-(4-methylbenzyl)isoxazolidin-3-one (0.2 g, 0.305 mmol) in MeOH (10 mL) was added Pd/C (0.2 g, 0.188 mmol) and stirred at RT under hydrogen balloon pressure for 16 h. The mixture was filtered through celite, the filterate was concentrated. The crude material was purified via preparative LC/MS with the following conditions: Waters Xbridge C18,19×150 mm, 5 μm; Guard Column:Waters XBridge C18,19×10 mm, 5 μm; Mobile Phase A:5:95 Methanol:water with 10 mM NH4OAc; Mobile Phase B: 95:5 Methanol:water with 10 mM NH4OAc; Gradient:15-60% B over 25 minutes, followed by a 10 minute hold at 60% B and 5 minute hold at 100% B; low:15 ml/min. Fractions containing the desired product were combined and dried using a Genevac centrifugal evaporator obtained 12 4-(4-(5-hydroxypyridin-2-yl)piperazin-1-yl)-2-(4-methylbenzyl)isoxazolidin-3-one (1.5 mg, 4.03 μmol, 1.320% yield). The racemic mixture was separated by Chiral HPLC/SFC to get P1 and P2.

H-NMR: 400 MHz, DMSO-d6: δ 2.30 (s, 3H), 2.56-2.61 (m, 2H), 2.91-2.96 (m, 2H), 3.28 (t, J=10.00 Hz, 4H), 3.82-3.85 (m, 1H), 4.23-4.27 (m, 1H), 4.36 (t, J=17.60 Hz, 1H), 4.62 (s, 2H), 6.72 (d, J=8.80 Hz, 1H), 7.06 (dd, J=12.00, Hz, 1H), 7.15-7.20 (m, 4H), 7.74 (d, J=2.80 Hz, 1H), 8.97 (s, 1H).

LCMS: A: 95% Water: 5% Acetonitrile; 10 mM NH4OAC, B: 5% Water:95% Acetonitrile; 10 mM NH4OAC Flow: 1.1 ml/min, Temp:50° C., Column: Ascentis Express C18 (50×2.1)mm, 2.7 μm, Time (min): 0 - - - 3, % B: 0 - - - 100, RT-1.229 min, (M+1)–369.

The compound 12 was separated by SFC obtained P1 4-(4-(5-hydroxypyridin-2-yl)piperazin-1-yl)-2-(4-methylbenzyl)isoxazolidin-3-one (4 mg, 10.31 μmol, 3.38% yield) and P2 4-(4-(5-hydroxypyridin-2-yl)piperazin-1-yl)-2-(4-methylbenzyl)isoxazolidin-3-one (6 mg, 0.015 mmol, 5.07% yield).

SFC Purification Method:

Analytical SFC Conditions: Column/dimensions: Chiralpak OJ-H(250×4.6)mm, 5 u, % CO2: 70%, % Co solvent: 30%(0.25% DEA in Methanol), Total Flow: 4.0 g/min, Back Pressure: 100 bar, Temperature: 25° C., UV: 220.

Preparative SFC Conditions: Column/dimensions: Chiralpak OJ-H(250×21)mm, 5 u, % CO2: 70%, % Co solvent: 30%(0.25% DEA in Methanol), Total Flow: 70.0 g/min, Back Pressure: 100 bar, Temperature: 25° C., UV: 220, Peak number: Retention Time::Peak 1:4.20::Peak 2:5.50::Solubility: 6 ml in Methanol, Loadability/Inj: 3.5 mg/mL, Total No of injections 15 Total Time for purification 2 hrs, Instrument details: Make/Model: Thar SFC-80.

For P1 (Homochiral):

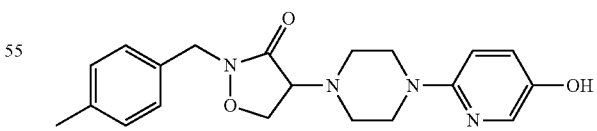

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, Time: % B::0.0:0.0::1.7:100.0::3.0:100.0::3.2:0.0, RT-2.209 min, (M+1)–369.

1H-NMR: 400 MHz, DMSO-d6: δ 2.29 (s, 3H), 2.56-2.59 (m, 2H), 2.91-2.94 (m, 2H), 3.27 (t, J=10.00 Hz, 4H), 3.81-3.84 (m, 1H), 4.22-4.26 (m, 1H), 4.35 (t, J=20.40 Hz,

1H), 4.61 (s, 2H), 6.71 (d, J=8.80 Hz, 1H), 7.05 (dd, J=12.40, Hz, 1H), 7.16-7.20 (m, 4H), 7.73 (d, J=2.80 Hz, 1H), 8.96 (s, 1H.

Chiral SFC: Injection Volume: 9, Co-Solvent: 0.3% DEA in Methanol, Column: Chiralcel OJ-H(4.6×250)mm, 5 u, Column Temperature: 23.9, Total Flow: 4, CO2 Flow Rate: 2.8, Co-Solvent Flow Rate: 1.2, Co-Solvent %: 30, Back Pressure: 100, RT-3.67 min.

For P2 (Homochiral):

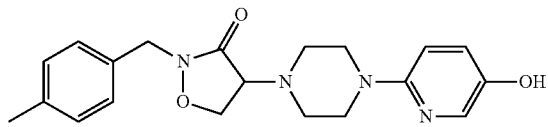 [SMILES: Cc1ccc(CN2OCC(N3CCN(c4ccc(O)cn4)CC3)C2=O)cc1]

LCMS: Column-Ascentis Express C18 (50×2.1 mm-2.7 µm), Mphase A: 10 mM NH4C00H IN, WATER:ACN(98: 02), Mphase B: 10 mM NH4C00H IN WATER:ACN(02: 98), Flow=1 ML/MIN, Time:% B::0.0:0.0::1.7:100.0::3.0: 100.0::3.2:0.0, RT-2.207 min; (M+1):369.

H-NMR: 400 MHz, DMSO-d6: δ 2.29 (s, 3H), 2.56-2.59 (m, 2H), 2.91-2.94 (m, 2H), 3.27 (t, J=10.00 Hz, 4H), 3.81-3.84 (m, 1H), 4.22-4.26 (m, 1H), 4.35 (t, J=20.40 Hz, 1H), 4.61 (s, 2H), 6.71 (d, J=8.80 Hz, 1H), 7.05 (dd, J=12.40, Hz, 1H), 7.16-7.20 (m, 4H), 7.73 (d, J=2.80 Hz, 1H), 8.96 (s, 1H).

Chiral SFC: Injection Volume: 9, Co-Solvent: 0.3% DEA in Methanol, Column: Chiralcel OJ-H(4.6×250)mm, 5 u, Column Temperature: 23.9, Total Flow: 4, CO2 Flow Rate: 2.8, Co-Solvent Flow Rate: 1.2, Co-Solvent %: 30, Back Pressure: 100, RT-4.63 min.

Example 11 (P1 and P2)

4-(3-fluoro-4-(3-fluoro-4-hydroxyphenyl)piperidin-1-yl)-2-(4-methylbenzyl)-1,2-oxazinan-3-one

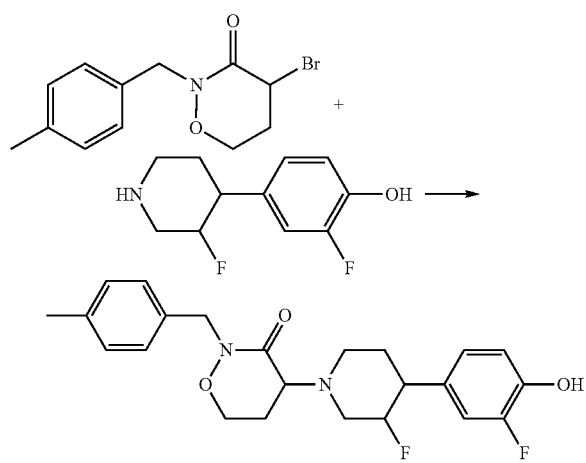

To a solution 2-fluoro-4-(3-fluoropiperidin-4-yl)phenol (0.1 g, 0.469 mmol) in DMF (3 mL) was added DIPEA (0.246 mL, 1.407 mmol) followed by 4-bromo-2-(4-methylbenzyl)-1,2-oxazinan-3-one (0.200 g, 0.703 mmol) then heated to 120° C. for 90 minutes in microwave. The mixture was allowed to cool to RT and then concentrated. The crude material was purified via preparative LC/MS with the following conditions: Waters Xbridge C18,19×150 mm, 5 µm; Guard Column: Waters XBridge C18,19×10 mm, 5 µm; Mobile Phase A:5:95 Acetonitrile:water with 10 mM NH4OAc; Mobile Phase B: 95:5 Acetonitrile: water with 10 mM NH4OAc; Gradient:15-50% B over 25 minutes, followed by a 10 minute hold at 50% B and 5 minute hold at 100% B; Flow:15 ml/min. Fractions containing the desired product were combined and dried using a Genevac centrifugal evaporator to obtain 11 4-(3-fluoro-4-(3-fluoro-4-hydroxyphenyl)piperidin-1-yl)-2-(4-methylbenzyl)-1,2-oxazinan-3-one (26 mg, 0.062 mmol, 13.31% yield). The diasteromeric mixture was separated by Chiral HPLC/SFC to get P1 and P2.

SFC Purification Condition:

Analytical SFC Conditions: Column/dimensions: Lux cellulose-2(250×4.6)mm, 5 u, % CO2: 60%, % Co solvent: 40%(0.25% DEA in Methanol), Total Flow: 4.0 g/min, Back Pressure: 100 bar, Temperature: 25° C., UV: 220.

Preparative SFC Conditions: Column/dimensions: Lux cellulose-2(250×21.5)mm, 5 u, % CO2: 60%, % Co solvent: 40%(0.25% DEA in Methanol), Total Flow: 75 g/min, Back Pressure: 100 bar, Temperature: 25° C. UV: 220, Peak number: Retention Time::Peak 1:3.50::Peak 2:4.10, Solubility: 10 ml in Methanol, Loadability/Inj: 3 mg/mL, Total No of injections 08, Total Time for purification 30 min. Instrument details: Make/Model: Thar SFC-80.

The compound 11 was separated by SFC to get P1; 4-(3-fluoro-4-(3-fluoro-4-hydroxyphenyl)piperidin-1-yl)-2-(4-methylbenzyl)-1,2-oxazinan-3-one (8 mg, 0.019 mmol, 4.05% yield) and P2, 4-(3-fluoro-4-(3-fluoro-4-hydroxyphenyl)piperidin-1-yl)-2-(4-methylbenzyl)-1,2-oxazinan-3-one (9 mg, 0.021 mmol, 4.56% yield).

For P1 (Homochiral):

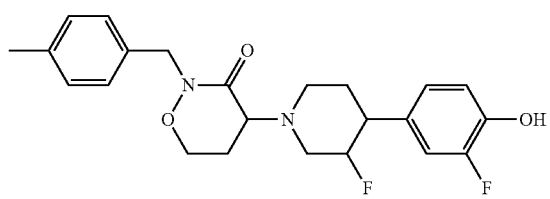 [SMILES: Cc1ccc(CN2OCCC(N3CCC(c4ccc(O)c(F)c4)C(F)C3)C2=O)cc1]

LCMS: Column-Ascentis Express C18 (50×2.1 mm-2.7 µm), Mphase A: 10 mM NH4C00H IN WATER:ACN(98: 02), Mphase B: 10 mM NH4C00H IN WATER:ACN(02: 98), Flow=1 ML/MIN, Time:% B::0.0:0.0::1.5:100.0::3.2: 100.0, RT-2.658 min; (M+1)–417.

H-NMR: 400 MHz, CDCl3: δ 1.78-1.87 (m, 2H), 2.04-2.10 (m, 1H), 2.30-2.35 (m, 4H), 2.59-2.64 (m, 1H), 2.73 (td, J=24.80, Hz, 1H), 2.86 (td, J=22.40, Hz, 1H), 2.99-3.01 (m, 1H), 3.31-3.33 (m, 1H), 3.65-3.70 (m, 1H), 3.93-3.97 (m, 1H), 3.99-4.04 (m, 1H), 4.50-4.63 (m, 1H), 4.72 (s, 2H), 6.94-6.96 (m, 2H), 7.01 (dd, J=12.00, Hz, 1H), 7.14 (d, J=7.60 Hz, 2H), 7.24 (d, J=8.00 Hz, 2H).

Chiral SFC: Injection Volume: 10, Co-Solvent: 0.3% DEA in Methanol, Column: Lux cellulose-2(4.6×250)mm, 5 u, Column Temperature: 24.9, Total Flow: 4, CO2 Flow Rate: 2.4, Co-Solvent Flow Rate: 1.6, Co-Solvent %: 40, Back Pressure: 101, RT-2.83 min.

For P2 (Homochiral):

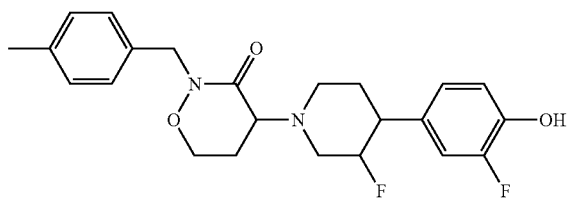 [SMILES: Cc1ccc(CN2OCCC(N3CCC(c4ccc(O)c(F)c4)C(F)C3)C2=O)cc1]

LCMS: Column-Ascentis Express C18 (50×2.1 mm-2.7 μm), Mphase A: 10 mM NH4C00H IN WATER:ACN(98: 02), Mphase B: 10 mM NH4C00H IN WATER:ACN(02: 98), Flow=1 ML/MIN, Time:% B::0.0:0.0::1.5:100.0::3.2: 100.0, RT-2.64 min, (M+1)–417.

H-NMR: 400 MHz, CDCl3: δ 1.78-1.88 (m, 2H), 2.05-2.08 (m, 1H), 2.31-2.35 (m, 4H), 2.60-2.69 (m, 2H), 2.81 (td, J=19.60, Hz, 1H), 2.91-2.94 (m, 1H), 3.41-3.44 (m, 1H), 3.64-3.71 (m, 1H), 3.93-3.97 (m, 1H), 3.99-4.04 (m, 1H), 4.53-4.67 (m, 1H), 4.72 (d, J=5.60 Hz, 2H), 6.92-6.96 (m, 2H), 6.98-7.02 (m, 1H), 7.14 (d, J=8.00 Hz, 2H), 7.24 (d, J=8.00 Hz, 2H).

Chiral SFC: Injection Volume: 10, Co-Solvent: 0.3% DEA in Methanol, Column: Lux cellulose-2(4.6×250)mm, 5 u, Column Temperature: 24.9, Total Flow: 4, CO2 Flow Rate: 2.4, Co-Solvent Flow Rate: 1.6, Co-Solvent %: 40, Back Pressure: 101, RT-3.33 min.

Example 12 (P1 & P2)

2-(4-chlorobenzyl)-4-((3S,4S)-3-fluoro-4-(4-hydroxyphenyl)piperidin-1-yl)-1,2-oxazinan-3-one

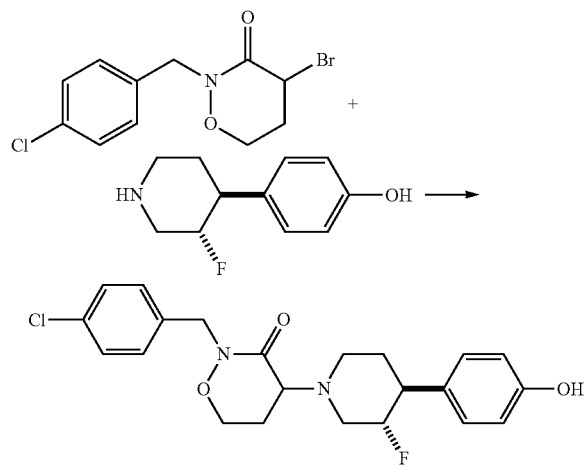

To a solution 4-((3S,4S)-3-fluoropiperidin-4-yl)phenol (0.1 g, 0.512 mmol) in DMF (2 mL) was added DIPEA (0.268 mL, 1.537 mmol) followed by 4-bromo-2-(4-chlorobenzyl)-1,2-oxazinan-3-one (0.234 g, 0.768 mmol) then heated to 120° C. for 90 minutes in microwave. The mixture was allowed to cool to RT and then concentrated. The crude material was purified via preparative LC/MS with the following conditions: Waters Xbridge C18,19×150 mm, 5 μm; Guard Column:Waters XBridge C18,19×10 mm, 5 μm; Mobile Phase A:5:95 Acetonitrile:water with 10 mM NH4OAc; Mobile Phase B: 95:5 Acetonitrile:water with 10 mM NH4OAc; Gradient:15-50% B over 25 minutes, followed by a 10 minute hold at 50% B and 5 minute hold at 100% B; Flow:15 ml/min. Fractions containing the desired product were combined and dried using a Genevac centrifugal evaporator to get 12 2-(4-chlorobenzyl)-4-((3S,4S)-3-fluoro-4-(4-hydroxyphenyl)piperidin-1-yl)-1,2-oxazinan-3-one (53 mg, 0.125 mmol, 24.45% yield). The diasteromeric mixture was separated by Chiral HPLC/SFC to get P1 and P2.

SFC Purification Condition:

Analytical SFC Conditions: Column/dimensions: Lux cellulose-2(250×4.6)mm, 5 u, % CO2: 60%, % Co solvent: 40%(0.25% DEA in Methanol), Total Flow: 4.0 g/min, Back Pressure: 100 bar, Temperature: 25° C., UV: 222.

Preparative SFC Conditions: Column/dimensions: Lux cellulose-2(250×21.5)mm, 5 u, % CO2: 60%, % Co solvent: 45%(0.25% DEA in Methanol), Total Flow: 75 g/min, Back Pressure: 100 bar, Temperature: 25° C., UV: 222, Peak number: Retention Time::Peak 1:3.90::Peak 2:4.80::Solubility: 10 ml in Methanol, Loadability/Inj: 5 mg/mL, Total No of injections 10 Total Time for purification 45 min, Instrument details: Make/Model: Thar SFC-80.

The compound 14 was separated by SFC obtained P1 2-(4-chlorobenzyl)-4-((3S,4S)-3-fluoro-4-(4-hydroxyphenyl)piperidin-1-yl)-1,2-oxazinan-3-one (17 mg, 0.040 mmol, 7.84% yield) and P2 2-(4-chlorobenzyl)-4-((3S,4S)-3-fluoro-4-(4-hydroxyphenyl)piperidin-1-yl)-1,2-oxazinan-3-one (15 mg, 0.035 mmol, 6.92% yield) as off white solid.

For P1 (Homochiral):

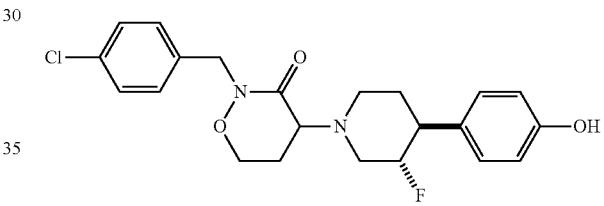

LCMS: Column-Ascentis Express C18 (50×2.1 mm-2.7 μm): Mphase A: 10 mM NH4C00H IN WATER:ACN(98: 02), Mphase B: 10 mM NH4C00H IN WATER:ACN(02: 98), Flow=1 ML/MIN, Time:% B::0.0:0.0::1.7:100.0::3.0: 100.0::3.2:0.0, RT-2.766 min, M(+1)–419.

H-NMR: 400 MHz, CDCl3: δ 1.84-1.87 (m, 2H), 2.06-2.12 (m, 1H), 2.32-2.36 (m, 1H), 2.61-2.74 (m, 2H), 2.84 (dt, J=25.60, Hz, 1H), 2.98-3.00 (m, 1H), 3.30-3.32 (m, 1H), 3.66-3.70 (m, 1H), 3.97-4.05 (m, 2H), 4.53-4.68 (m, 1H), 4.72 (s, 2H), 6.80 (d, J=8.40 Hz, 2H), 7.14 (d, J=8.80 Hz, 2H), 7.27-7.33 (m, 4H).

Chiral SFC: Injection Volume: 10, Co-Solvent: 0.3% DEA in Methanol, Column: Lux cellulose-2(4.6×250)mm, 5 u, Column Temperature: 24.7, Total Flow: 4, CO2 Flow Rate: 2.4, Co-Solvent Flow Rate: 1.6, Co-Solvent %: 40, Back Pressure: 101, RT-3.7 min.

For P2 (Homochiral):

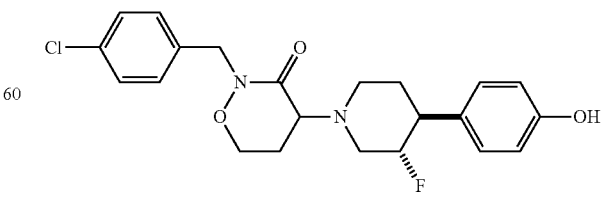

LCMS: Column-Ascentis Express C18 (50×2.1 mm-2.7 μm), Mphase A: 10 mM NH4C00H IN WATER:ACN(98: 02), Mphase B: 10 mM NH4C00H IN WATER:ACN(02:

98), Flow=1 ML/MIN, Time:% B::0.0:0.0::1.7:100.0::3.0: 100.0::3.2:0.0, RT-2.762 min, (M+1)–419.

H-NMR: 400 MHz, CDCl3: δ 1.85-1.88 (m, 2H), 2.04-2.10 (m, 1H), 2.32-2.37 (m, 1H), 2.64 (dt, J=26.40, Hz, 2H), 2.79 (dt, J=24.40, Hz, 2H), 2.92 (d, J=10.80 Hz, 1H), 3.40-3.43 (m, 1H), 3.64-3.69 (m, 1H), 3.95-4.06 (m, 2H), 4.56-4.68 (m, 1H), 4.69 (s, 2H), 6.80 (d, J=8.40 Hz, 2H), 7.14 (d, J=8.80 Hz, 2H), 7.27-7.33 (m, 4H).

Chiral SFC: Injection Volume: 10, Co-Solvent: 0.3% DEA in Methanol, Column: Lux cellulose-2(4.6×250)mm, 5 u, Column Temperature: 24.7, Total Flow: 4, CO2 Flow Rate: 2.4, Co-Solvent Flow Rate: 1.6, Co-Solvent %: 40, Back Pressure: 101, RT-4.57 min.

Example 13 (P1 & P2)

4-(3-fluoro-4-(3-fluoro-4-hydroxyphenyl)piperidin-1-yl)-2-(4-fluorobenzyl)-1,2-oxazinan-3-one

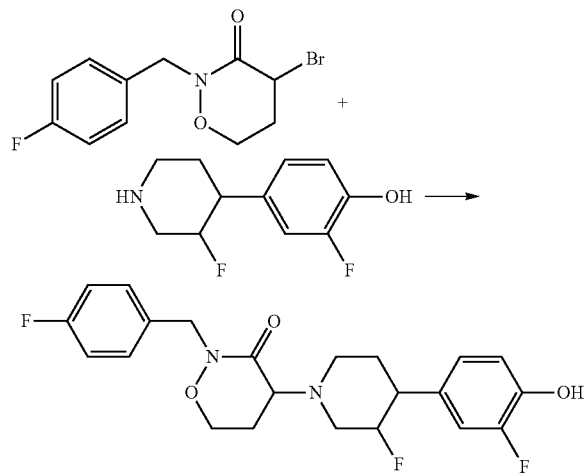

To a solution of 2-fluoro-4-(3-fluoropiperidin-4-yl)phenol (0.1 g, 0.469 mmol) in DMF (2 mL) was added DIPEA (0.246 mL, 1.407 mmol) followed by 4-bromo-2-(4-fluorobenzyl)-1,2-oxazinan-3-one (0.203 g, 0.703 mmol) then heated to 120° C. for 90 minutes.in microwave. The mixture was allowed to cool to RT and then concentrated. The crude material was purified via preparative LC/MS with the following conditions: Waters Xbridge C18,19×150 mm, 5 μm; Guard Column:Waters XBridge C18,19×10 mm, 5 μm; Mobile Phase A:5:95 Acetonitrile:water with 10 mM NH4OAc; Mobile Phase B: 95:5 Acetonitrile:water with 10 mM NH4OAc; Gradient:15-50% B over 25 minutes, followed by a 10 minute hold at 50% B and 5 minute hold at 100% B; Flow:15 ml/min. Fractions containing the desired product were combined and dried using a Genevac centrifugal evaporator to obtain 13 4-(3-fluoro-4-(3-fluoro-4-hydroxyphenyl)piperidin-1-yl)-2-(4-fluorobenzyl)-1,2-oxazinan-3-one (23 mg, 0.054 mmol, 11.43% yield). The diasteromeric mixture was separated by Chiral HPLC/SFC to get P1 and P2.

SFC Purification Method:

Analytical SFC Conditions: Column/dimensions: Chiralpak AD-H(250×4.6)mm, 5 u, % CO2: 60%, % Co solvent: 40%(0.25% DEA in Methanol), Total Flow: 4.0 g/min., Back Pressure: 100 bar, Temperature: 25° C., UV: 220.

Preparative SFC Conditions: Column/dimensions: Chiralpak AD-H(250×21)mm, 5 u, % CO2: 60%, % Co solvent: 45%(0.25% DEA in Methanol), Total Flow: 75 g/min, Back Pressure: 100 bar, Temperature: 25° C., UV: 220, Peak number: Retention Time::Peak 1:4.60::Peak 2:6.00. Solubility: 10 ml in Methanol, Loadability/Inj: 2 mg/mL, Total No of injections 09 Total Time for purification 1 hrs, Instrument details: Make/Model: Thar SFC-80.

The compound 15 was separated by SFC obtained P1 4-(3-fluoro-4-(3-fluoro-4-hydroxyphenyl)piperidin-1-yl)-2-(4-fluorobenzyl)-1,2-oxazinan-3-one (6 mg, 0.014 mmol, 3.01% yield) and P2 4-(3-fluoro-4-(3-fluoro-4-hydroxyphenyl)piperidin-1-yl)-2-(4-fluorobenzyl)-1,2-oxazinan-3-one (6 mg, 0.014 mmol, 3.01% yield) as off white solid.

For P1 (Homochiral):

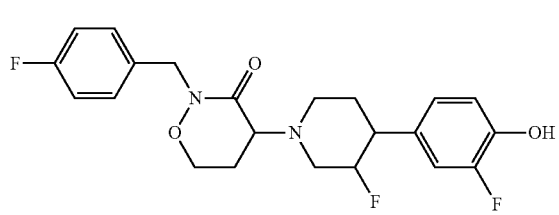

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, Time:% B::0.0:0.0::1.7:100.0::3.0:100.0::3.2:0.0, RT-2.697 min, (M(+1)–421.

H-NMR: 400 MHz, CDCl3: δ 1.78-1.88 (m, 2H), 2.03-2.09 (m, 1H), 2.32-2.36 (m, 1H), 2.60-2.68 (m, 2H), 2.81 (dt, J=24.40, Hz, 1H), 2.90-2.94 (m, 1H), 3.40-3.43 (m, 1H), 3.63-3.68 (m, 1H), 3.93-4.05 (m, 2H), 4.51-4.65 (m, 1H), 4.66 (s, 2H), 6.94-7.04 (m, 5H), 7.31-7.34 (m, 2H).

Chiral SFC: Injection Volume: 10, Co-Solvent: 0.3% DEA in Methanol, Column: Chiralpak AD H (250×4.6)mm 5 u, Column Temperature: 24.6, Total Flow: 4, CO2 Flow Rate: 2.4, Co-Solvent Flow Rate: 1.6, Co-Solvent %: 40, Back Pressure: 99, RT-4.37 min.

For P2 (Homochiral):

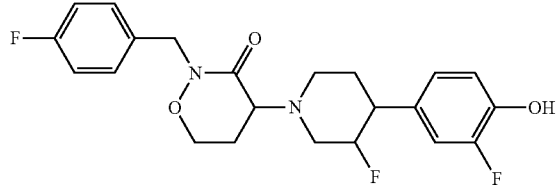 [SMILES: O=C1C(N2CCC(c3ccc(O)c(F)c3)C(F)C2)CCON1Cc1ccc(F)cc1]

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, Time:% B::0.0:0.0::1.7:100.0::3.0:100.0::3.2:0.0, RT-2.702 min; (M+1)–421.

H-NMR: 400 MHz, CDCl3: δ 1.78-1.88 (m, 2H), 2.05-2.11 (m, 1H), 2.31-2.36 (m, 1H), 2.63 (dt, J=22.40, Hz, 1H), 2.72 (dt, J=24.80, Hz, 1H), 2.86 (dt, J=25.60, Hz, 1H), 2.98-3.00 (m, 1H), 3.30-3.32 (m, 1H), 3.65-3.69 (m, 1H), 3.95-4.05 (m, 2H), 4.49-4.62 (m, 1H), 4.71 (s, 2H), 6.94-7.05 (m, 5H), 7.31-7.34 (m, 2H).

Chiral SFC: Injection Volume: 10, Co-Solvent: 0.3% DEA in Methanol, Column: Chiralpak AD H (250×4.6)mm 5 u, Column Temperature: 24.6, Total Flow: 4, CO2 Flow Rate: 2.4, Co-Solvent Flow Rate: 1.6, Co-Solvent %: 40, Back Pressure: 99, RT-5.8 min.

Example 14 (P1 & P2)

2-(4-chlorobenzyl)-4-(3-fluoro-4-(3-fluoro-4-hydroxyphenyl)piperidin-1-yl)-1,2-oxazinan-3-one

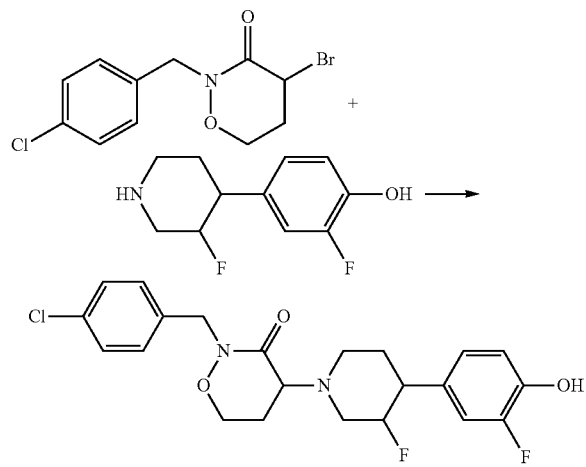

To a solution 2-fluoro-4-(3-fluoropiperidin-4-yl)phenol (0.1 g, 0.469 mmol) in DMF (2 mL) was added DIPEA (0.246 mL, 1.407 mmol) followed by 4-bromo-2-(4-chlorobenzyl)-1,2-oxazinan-3-one (0.214 g, 0.703 mmol) then heated to 120° C. for 90 minutes in microwave. The mixture was allowed to cool to RT. Then concentrated. The crude material was purified via preparative LC/MS with the following conditions: Waters Xbridge C18,19×150 mm, 5 μm; Guard Column:Waters XBridge C18,19×10 mm, 5 μm; Mobile Phase A:5:95 Acetonitrile:water with 10 mM NH4OAc; Mobile Phase B: 95:5 Acetonitrile:water with 10 mM NH4OAc; Gradient:15-50% B over 25 minutes, followed by a 10 minute hold at 50% B and 5 minute hold at 100% B; Flow:15 ml/min. Fractions containing the desired product were combined and dried using a Genevac centrifugal evaporator to obtain 14; 2-(4-chlorobenzyl)-4-(3-fluoro-4-(3-fluoro-4-hydroxyphenyl)piperidin-1-yl)-1,2-oxazinan-3-one (45 mg, 0.093 mmol, 19.77% yield). The diasteromeric mixture was separated by Chiral HPLC/SFC to get P1 and P2.

SFC Purification Condition:

Analytical SFC Conditions: Column/dimensions: Chiralpak OJ-H(250×4.6)mm, 5 u, % CO2: 70%, % Co solvent: 30%(0.25% DEA in Methanol), Total Flow: 3.0 g/min, Back Pressure: 100 bar, Temperature: 25° C., UV: 220, Preparative SFC Conditions: Column/dimensions: Chiralpak OJ-H(250×21)mm, 5 u, % CO2: 70%, % Co solvent: 30%(0.25% DEA in Methanol), Total Flow: 60 g/min, Back Pressure: 100 bar, Temperature: 25° C., UV: 220, Peak number: Retention Time::Peak 1:6.00::Peak 2:7.50, Solubility: 20 ml in Methanol, Loadability/Inj: 2 mg/mL, Total No of injections 18. Total Time for purification 2 hrs, Instrument details: Make/Model: Thar SFC-80

The compound 16 was separated by SFC obtained P1; 2-(4-chlorobenzyl)-4-(3-fluoro-4-(3-fluoro-4-hydroxyphenyl)piperidin-1-yl)-1,2-oxazinan-3-one (11 mg, 0.025 mmol, 5.26% yield) and P2; 2-(4-chlorobenzyl)-4-(3-fluoro-4-(3-fluoro-4-hydroxyphenyl)piperidin-1-yl)-1,2-oxazinan-3-one (13 mg, 0.029 mmol, 6.22% yield).

For P1 (Homochiral):

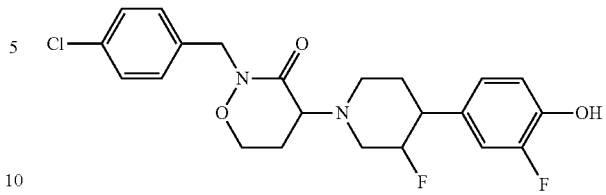

LCMS: Column-Ascentis Express C8 (50×2.1 mm-2.7 μm), Mphase A: 2% ACN-98% H20-10 mM NH4C00H Mphase B: 98% ACN-2% H20-10 mM NH4C00H, Flow=1 ML/MIN, Time:% B::0.0:0.0::1.7:100.0::4.0:100.0, RT-1.981 min, M+1)–437.

H-NMR: 400 MHz, CDCl3: δ 1.79-1.88 (m, 2H), 2.04-2.10 (m, 1H), 2.32-2.37 (m, 1H), 2.61-2.68 (m, 2H), 2.81 (dt, J=24.40, Hz, 1H), 2.90-2.94 (m, 1H), 3.40-3.43 (m, 1H), 3.64-3.68 (m, 1H), 3.96-4.06 (m, 2H), 4.52-4.64 (m, 1H), 4.72 (s, 2H), 6.92-7.02 (m, 3H), 7.27-7.33 (m, 4H).

Chiral SFC: Injection Volume: 10, Co-Solvent: 0.3% DEA in Methanol, Column: Chiralcel OJ-H(4.6×250)mm, 5 u, Column Temperature: 24.4, Total Flow: 3, CO2 Flow Rate: 2.1, Co-Solvent Flow Rate: 0.9, Co-Solvent %: 30, Back Pressure: 100, RT-6.01 min.

For P2 (Homochiral):

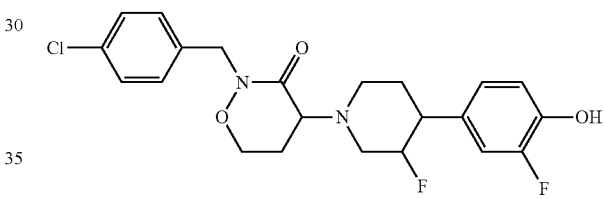

H-NMR: 400 MHz, CDCl3: δ 1.78-1.88 (m, 2H), 2.05-2.11 (m, 1H), 2.32-2.36 (m, 1H), 2.60-2.75 (m, 2H), 2.84-2.89 (m, 1H), 2.98 (d, J=2.00 Hz, 1H), 3.30-3.32 (m, 1H), 3.65-3.70 (m, 1H), 3.96-4.05 (m, 2H), 4.51-4.68 (m, 1H), 4.74 (s, 2H), 6.92-7.02 (m, 3H), 7.25-7.31 (m, 4H).

LCMS: Column-Ascentis Express C8 (50×2.1 mm-2.7 μm), Mphase A: 2% ACN-98% H20-10 mM NH4C00H Mphase B: 98% ACN-2% H20-10 mM NH4C00H, Flow=1 ML/MIN, Time:% B::0.0:0.0::1.7:100.0::4.0:100.0, RT-1.995 min; (M+1)–437.

Chiral SFC: Injection Volume: 10, Co-Solvent: 0.3% DEA in Methanol, Column: Chiralcel OJ-H(4.6×250)mm, 5 u, Column Temperature: 24.4, Total Flow: 3, CO2 Flow Rate: 2.1, Co-Solvent Flow Rate: 0.9, Co-Solvent %: 30, Back Pressure: 100, RT-7.11 min.

Example 15 (P1 & P2)

4-((3S,4S)-3-fluoro-4-(4-hydroxyphenyl)piperidin-1-yl)-2-(4-fluorobenzyl)-1,2-oxazinan-3-one

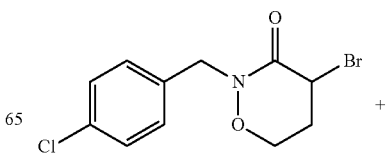

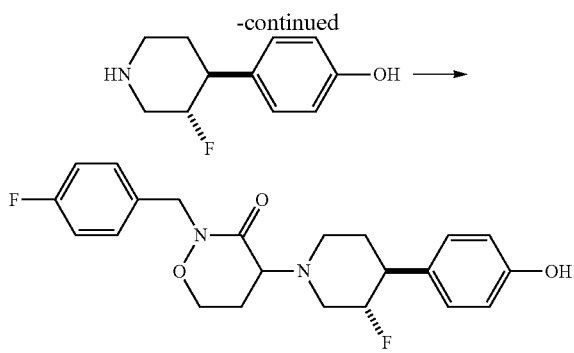

To a solution of 4-((3S,4S)-3-fluoropiperidin-4-yl)phenol (0.1 g, 0.512 mmol) in DMF (2 mL) was added DIPEA (0.268 mL, 1.537 mmol) followed by 4-bromo-2-(4-fluorobenzyl)-1,2-oxazinan-3-one (0.221 g, 0.768 mmol) then heated to 120° C. for 90 minutes in microwave. The mixture was allowed to cool to RT and then concentrated. The crude material was purified via preparative LC/MS with the following conditions: Waters Xbridge C18,19×150 mm, 5 μm; Guard Column:Waters XBridge C18,19×10 mm, 5 μm; Mobile Phase A:5:95 Acetonitrile:water with 10 mM NH4OAc; Mobile Phase B: 95:5 Acetonitrile:water with 10 mM NH4OAc; Gradient:15-50% B over 25 minutes, followed by a 10 minute hold at 50% B and 5 minute hold at 100% B; Flow:15 ml/min. Fractions containing the desired product were combined and dried using a Genevac centrifugal evaporator to obtained 15; 4-((3S,4S)-3-fluoro-4-(4-hydroxyphenyl)piperidin-1-yl)-2-(4-fluorobenzyl)-1,2-oxazinan-3-one (51 mg, 0.115 mmol, 22.51% yield). The diasteromeric mixture was separated by Chiral HPLC/SFC to get P1 and P2.

SFC Purification Method:

Analytical SFC Conditions: Column/dimensions: Chiralpak OJ-H(250×4.6)mm, 5 u, % CO2: 70%, % Co solvent: 30%(0.25% DEA in Methanol), Total Flow: 3.0 g/min, Back Pressure: 100 bar, Temperature: 25° C., UV: 222, Preparative SFC Conditions: Column/dimensions: Chiralpak OJ-H(250×21)mm, 5 u, % CO2: 70%, % Co solvent: 30%(0.25% DEA in Methanol), Total Flow: 60 g/min, Back Pressure: 100 bar, Temperature: 25° C., UV: 222, Peak number: Retention Time::Peak 1:6.00::Peak 2:7.20, Solubility: 15 ml in Methanol, Loadability/Inj: 3 mg/mL, Total No of injections 15 Total Time for purification 45 min, Instrument details: Make/Model: Thar SFC-80.

The compound 15 was separated by SFC to obtained P1; 4-((3S,4S)-3-fluoro-4-(4-hydroxyphenyl)piperidin-1-yl)-2-(4-fluorobenzyl)-1,2-oxazinan-3-one (9 mg, 0.022 mmol, 4.32% yield) and P2; 4-((3S,4S)-3-fluoro-4-(4-hydroxyphenyl)piperidin-1-yl)-2-(4-fluorobenzyl)-1,2-oxazinan-3-one (9 mg, 0.022 mmol, 4.28% yield).

For P1 (Homochiral):

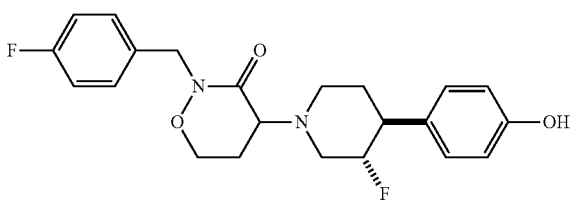 [SMILES: O=C1C(N2CC[C@@H](c3ccc(O)cc3)[C@H](F)C2)CCON1Cc1ccc(F)cc1]

LCMS: Column-Ascentis Express C8 (50×2.1 mm-2.7 μm), Mphase A: 2% ACN-98% H20-10 mM NH4C00H Mphase B: 98% ACN-2% H20-10 mM NH4C00H, Flow=1 ML/MIN, Time:% B::0.0:0.0::1.7:100.0::4.0:100.0, RT-1.925 min, (M+1)–403.

H-NMR: 400 MHz, CDCl3: δ 1.84-1.88 (m, 2H), 2.04-2.10 (m, 1H), 2.32-2.37 (m, 1H), 2.64 (dt, J=26.40, Hz, 1H), 2.79 (dt, J=24.40, Hz, 1H), 2.92 (d, J=10.80 Hz, 1H), 3.41-3.43 (m, 1H), 3.64-3.68 (m, 1H), 3.94-4.06 (m, 2H), 4.56-4.70 (m, 1H), 4.72 (s, 2H), 6.80 (td, J=14.40, Hz, 2H), 7.15 (td, J=14.00, Hz, 2H), 7.31-7.35 (m, 2H).

Chiral SFC: Injection Volume: 10, Co-Solvent: 0.3% DEA in Methanol, Column: Chiralcel OJ-H(4.6×250)mm, 5 u, Column Temperature: 24.3, Total Flow: 3, CO2 Flow Rate: 2.1, Co-Solvent Flow Rate: 0.9, Co-Solvent %: 30, Back Pressure: 101, RT-5.86 min.

For P2 (Homochiral):

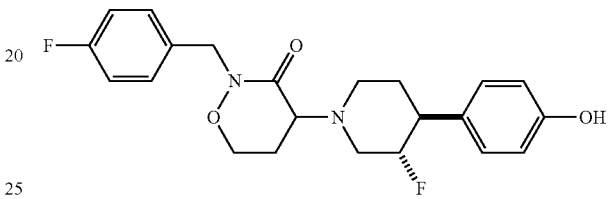

LCMS: Column-Ascentis Express C8 (50×2.1 mm-2.7 μm), Mphase A: 2% ACN-98% H20-10 mM NH4C00H Mphase B: 98% ACN-2% H20-10 mM NH4C00H, Flow=1 ML/MIN, Time:% B::0.0:0.0::1.7:100.0::4.0:100.0, RT-1.923 min, (M+1)–403.

H-NMR: 400 MHz, CDCl3: δ 1.81-1.87 (m, 2H), 2.06-2.12 (m, 1H), 2.32-2.36 (m, 1H), 2.61-2.66 (m, 1H), 2.71 (dt, J=24.40, Hz, 1H), 2.84 (dt, J=22.40, Hz, 1H), 2.99 (d, J=10.40 Hz, 1H), 3.30-3.33 (m, 1H), 3.65-3.70 (m, 1H), 3.95-4.05 (m, 2H), 4.53-4.66 (m, 1H), 4.72 (s, 2H), 6.80 (d, J=8.80 Hz, 2H), 7.00-7.05 (m, 2H), 7.15 (d, J=8.40 Hz, 2H), 7.31-7.34 (m, 2H).

Chiral SFC: Injection Volume: 10, Co-Solvent: 0.3% DEA in Methanol, Column: Chiralcel OJ-H(4.6×250)mm, 5 u, Column Temperature: 24.3, Total Flow: 3, CO2 Flow Rate: 2.1, Co-Solvent Flow Rate: 0.9, Co-Solvent %: 30, Back Pressure: 101, RT-6.73 min.

Biological Methods

Radioligand Binding Assay. Binding experiments to determine binding to NR2B-subtype NMDA receptors were performed on forebrains of 8-10 weeks old male Sprague Dawley rats (Harlan, Netherlands) using [3]H Ro 25-6981 (Mutel V; Buchy D; Klingelschmidt A; Messer J; Bleuel Z; Kemp J A; Richards J G. Journal of Neurochemistry, 1998, 70(5):2147-2155. Rats were decapitated without anesthesia using a Guillotine (approved by animal ethics committee) and the harvested brains were snap-frozen and stored at −80° C. for 3-6 months for membrane preparation.

For membrane preparation, rat forebrains were thawed on ice for 20 minutes in homogenization buffer composed of 50 mM $KH_2PO_4$ (pH adjusted to 7.4 with KOH), 1 mM EDTA, 0.005% Triton X 100 and protease inhibitor cocktail (Sigma Aldrich). Thawed brains were homogenized using a Dounce homogenizer and centrifuged at 48000×g for 20 min. The pellet was resuspended in cold buffer and homogenized again using a Dounce homogenizer. Subsequently, the homogenate was aliquoted, snap-frozen and stored at −80° C. for not more than 3-4 months.

To perform the competition binding assay, thawed membrane homogenate was added to each well of a 96-well plate (20 μg/well). The experimental compounds were serially diluted in 100% DMSO and added to each row of the assay plate to achieve desired compound concentrations, keeping the DMSO concentration in the assay plate at 1.33% of the final reaction volume. Next, $^3$H Ro 25-6981 (4 nM) was added to the assay plate. After incubation for 1 hr at room temperature, the membrane bound radioligand was harvested on to GF/B filter plates (treated with 0.5% PEI for 1 hr at room temperature). The filter plates were dried at 50° C. for 20 mins, incubated with microscint 20 for 10 minutes and finally, the counts were read on TopCount (Perkin Elmer). Non-specific binding was determined using MK-0657 (the preparation of this compound is described as example 1 in WO 2004 108705 (40 μM). CPM values were converted to % inhibition and the concentration response curves were plotted using custom made software. Each experiment was repeated at least twice to obtain the final binding $K_i$ values for experimental compounds. Using this assay, the compound of example 10 P-1 shows a binding Ki of 3.2 nM.

| Example | Structure | NR2B Binding Ki, nM |
|---|---|---|
| 1, P-1 | 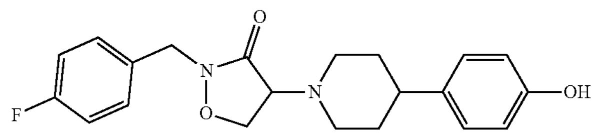 [SMILES: O=C1C(N2CCC(c3ccc(O)cc3)CC2)CON1Cc1ccc(F)cc1] | 304.90 |
| 1, P-2 | 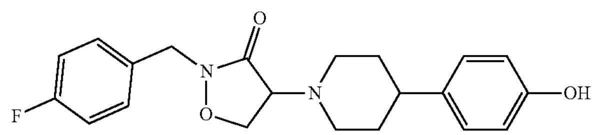 [SMILES: O=C1C(N2CCC(c3ccc(O)cc3)CC2)CON1Cc1ccc(F)cc1] | 4.08 |
| 2, P-1 | 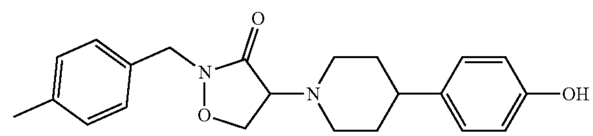 [SMILES: Cc1ccc(CN2OCC(N3CCC(c4ccc(O)cc4)CC3)C2=O)cc1] | 112.30 |
| 2, P-2 | 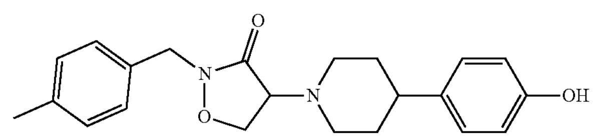 [SMILES: Cc1ccc(CN2OCC(N3CCC(c4ccc(O)cc4)CC3)C2=O)cc1] | 2.79 |
| 3 | 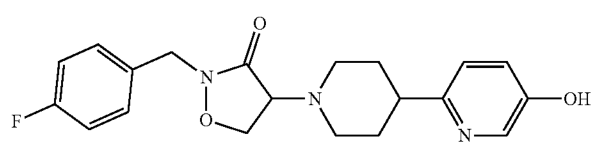 [SMILES: O=C1C(N2CCC(c3ccc(O)cn3)CC2)CON1Cc1ccc(F)cc1] | 15.08 |
| 4 | 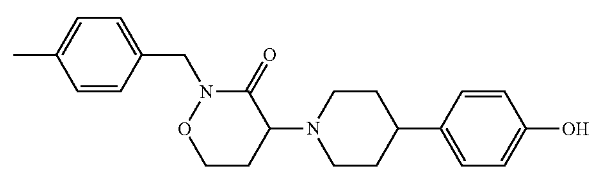 [SMILES: Cc1ccc(CN2OCCC(N3CCC(c4ccc(O)cc4)CC3)C2=O)cc1] | 5.49 |
| 5, P-1 | 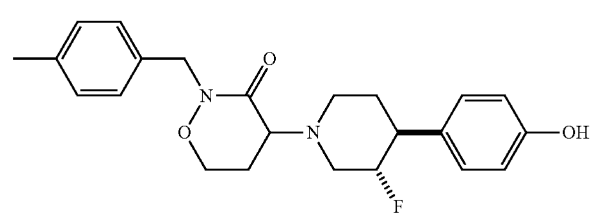 [SMILES: Cc1ccc(CN2OCCC(N3CC[C@@H](c4ccc(O)cc4)[C@H](F)C3)C2=O)cc1] | 143.70 |

-continued

| Example | Structure | NR2B Binding Ki, nM |
|---|---|---|
| 5, P-2 | 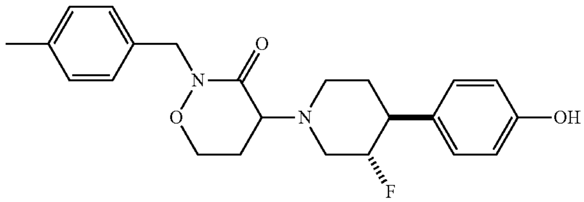 [SMILES: Cc1ccc(CN2OCCC(N3CC[C@@H](c4ccc(O)cc4)[C@H](F)C3)C2=O)cc1] | 4.37 |
| 6, P-1 | 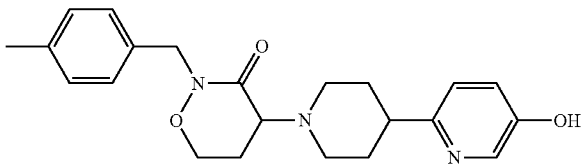 | 6.53 |
| 6, P-2 | 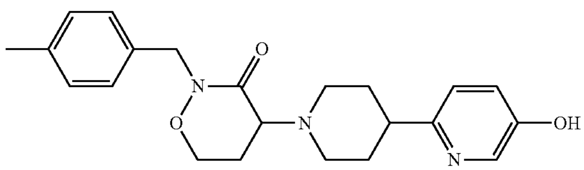 | 8.16 |
| 7, P-1 | 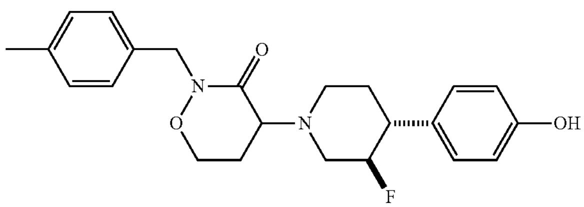 [SMILES: Cc1ccc(CN2OCCC(N3CC[C@H](c4ccc(O)cc4)[C@@H](F)C3)C2=O)cc1] | 124.80 |
| 7, P-2 | 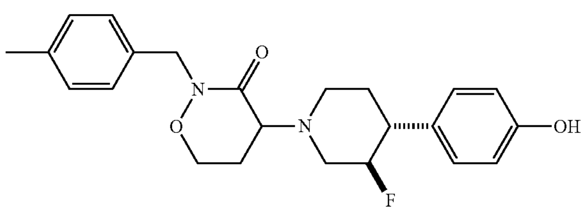 [SMILES: Cc1ccc(CN2OCCC(N3CC[C@H](c4ccc(O)cc4)[C@@H](F)C3)C2=O)cc1] | 4.98 |
| 8, P-1 | 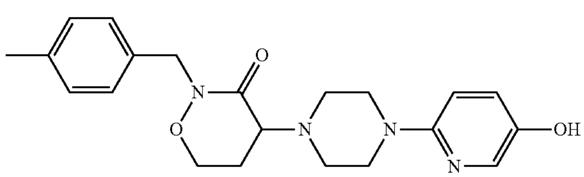 | 57.82 |
| 8, P-2 | 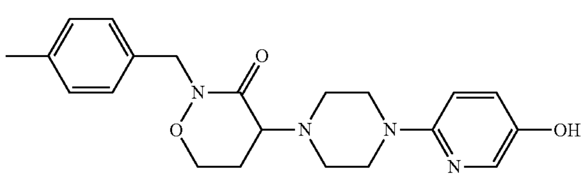 | 18.75 |
| 9, P-1 | 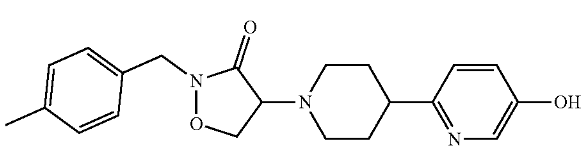 | 139.40 |

-continued

| Example | Structure | NR2B Binding Ki, nM |
|---|---|---|
| 9, P-2 | 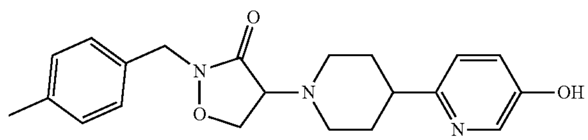 [SMILES: Cc1ccc(CN2OCC(N3CCC(c4ccc(O)cn4)CC3)C2=O)cc1] | 12.08 |
| 10, P-1 | 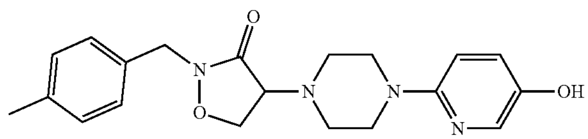 | 3.20 |
| 10, P-2 | 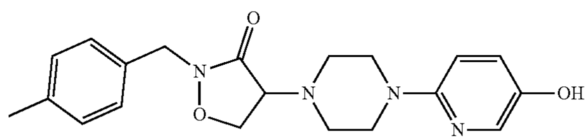 | 10.70 |
| 11, P-1 | 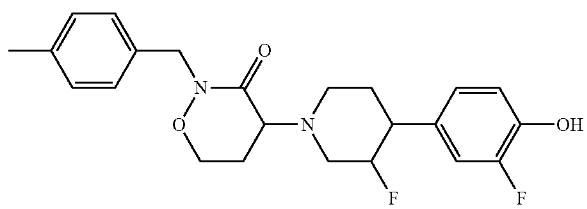 [SMILES: Cc1ccc(CN2OCCC(N3CCC(c4ccc(O)c(F)c4)C(F)C3)C2=O)cc1] | 3.06 |
| 11, P-2 | 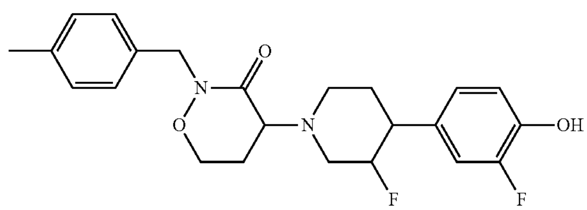 [SMILES: Cc1ccc(CN2OCCC(N3CCC(c4ccc(O)c(F)c4)C(F)C3)C2=O)cc1] | 39.34 |
| 12, P-1 | 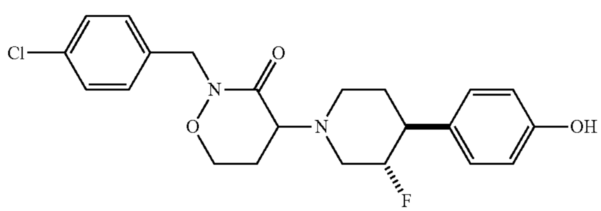 [SMILES: O=C1C(N2CC[C@@H](c3ccc(O)cc3)[C@H](F)C2)CCON1Cc1ccc(Cl)cc1] | 3.90 |
| 12, P-2 | 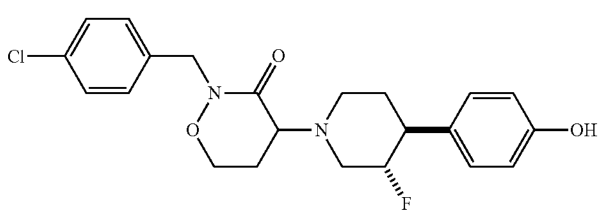 [SMILES: O=C1C(N2CC[C@@H](c3ccc(O)cc3)[C@H](F)C2)CCON1Cc1ccc(Cl)cc1] | 149.70 |
| 13, P-1 | 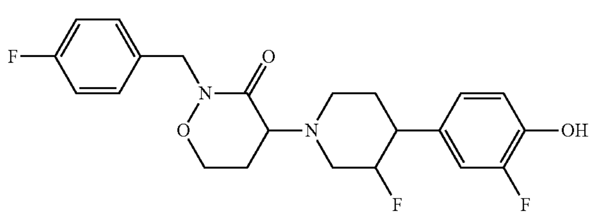 [SMILES: O=C1C(N2CCC(c3ccc(O)c(F)c3)C(F)C2)CCON1Cc1ccc(F)cc1] | 367.20 |

-continued

| Example | Structure | NR2B Binding Ki, nM |
|---|---|---|
| 13, P-2 | 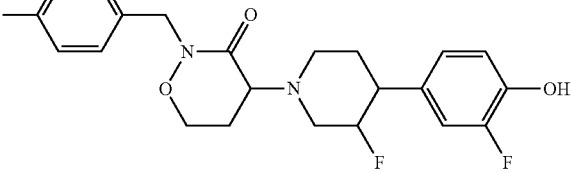 | 4.03 |
| 14, P-1 | 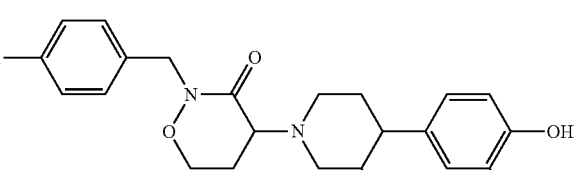 | 98.68 |
| 14, P-2 | 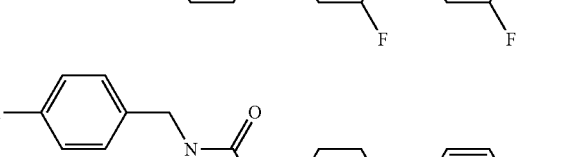 | 2.80 |
| 15, P-1 | 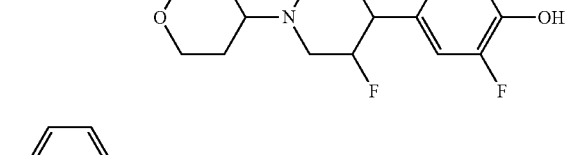 | 393.00 |
| 15, P-2 | 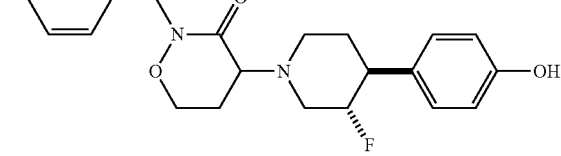 | 12.54 |

Ex Vivo Occupancy Assay. This assay demonstrates that the compound of example 2P-2 occupies brain-resident NR2B-subtype receptors in animals after dosing. 7-9 weeks old male CD-1 mice were dosed intravenously in a vehicle consisting of 10% dimethylacetamide, 40% PEG-400, 30% hydroxypropyl betacyclodextrin, and 30% water with experimental compounds and the forebrains were harvested 15 minutes post-dosing by decapitation. The brain samples were immediately snap-frozen and stored at −80° C. On the following day, the dosed brain samples were thawed on ice for 15-20 minutes followed by homogenization using Polytron for 10 seconds in cold homogenization buffer composed of 50 mM $KH_2PO_4$ (pH adjusted to 7.4 with KOH), 1 mM EDTA, 0.005% Triton X 100 and protease inhibitor cocktail (Sigma Aldrich). The crude homogenates were further homogenized using a Dounce homogenizer and the homogenized membrane aliquots from all animals were flash-frozen and stored at −80° C. until further use. The whole homogenization process was performed on ice. For determining occupancy, the membrane homogenates were first thawed on ice and then needle-homogenized using a 25 gauge needle. The homogenized membrane (6.4 mg/ml) was added to a 96-well plate followed by addition of $^3$H Ro 25-6981 (6 nM). The reaction mixture was incubated for 5 minutes on a shaker at 4° C. and then harvested onto GF/B filter plates (treated with 0.5% PEI for 1 hr at room temperature). The filter plates were dried at 50° C. for 20 mins, incubated with microscint 20 for 10 minutes and read on TopCount (Perkin Elmer). Each dose or compound group consisted of 4-5 animals. The control group of animals was dosed with vehicle alone. Membrane from each animal was added in triplicates to the assay plate. Non-specific binding was determined using 10 μM Ro 25-6981 added to the wells containing membrane homogenates from vehicle-dosed animals. Specific counts/minute was converted to % occupancy at each dose of a compound for each animal using the following equation:

$$\% \text{ Occupancy (animal } A\text{)} = 100 - \left( \frac{\text{specific CPM of animal } A}{\text{Average CPM from control group}} \times 100 \right)$$

Using this procedure, the compound of example 10, P-1 shows 94% NR2B receptor occupancy after a 3 mg/Kg i.v. dose. Drug levels were determined by mass spectroscopy in the usual manner. Drug levels in the blood plasma were 572 nM in at this dose, and drug levels in the homogenized brain tissue were 863 nM.

hERG Electrophysiology Assay. The experimental compounds were assessed for hERG activity on HEK 293 cells stably expressing hERG channels using patch clamp technique. Coverslips plated with hERG expressing cells were placed in the experimental chamber and were perfused with a solution composed of (in mM): 140 NaCl, 4 KCl, 1.8 $CaCl_2$, 1 $MgCl_2$, 10 Glucose, 10 HEPES (pH 7.4, NaOH) at room temperature. Borosilicate patch pipettes had tip resistances of 2-4 Mohms when filled with an internal solution containing: 130 KCl, 1 $MgCl_2$, 1 $CaCl_2$, 10 EGTA, 10 HEPES, 5 ATP-$K_2$ (pH 7.2, KOH). The cells were clamped at −80 mV in whole cell configuration using an Axopatch 200B (Axon instruments, Union City, Calif.) patch clamp amplifier controlled by pClamp (Axon instruments) software. Upon formation of a gigaseal, the following voltage protocol was repeatedly (0.05 Hz) applied to record tail currents: depolarization step from −80 mV to +20 mV for 2 seconds followed by a hyperpolarization step to −65 mV (3 seconds) to elicit tail currents and then, back to the holding potential. Compounds were applied after stabilization of tail current. First, tail currents were recorded in presence of extracellular solution alone (control) and subsequently, in extracellular solution containing increasing compound concentrations. Each compound concentration was applied for 2-5 minutes. The percentage inhibition at each concentration was calculated as reduction in peak tail current with respect to the peak tail current recorded in the presence of control solution. Data analysis was performed in custom made software. The percent inhibitions at different concentrations were plotted to obtain a concentration response curve, which was subsequently fitted with a four parameter equation to calculate the hERG $IC_{50}$ value. Using this procedure, the compound of example 10,P-1 is a poor inhiibitor of the hERG channel, with an $IC_{50}$=30 μM.

Mouse Forced Swim Test (mFST). Forced Swim Test (FST) is an animal model used to assess antidepressant compounds in preclinical studies. The FST was performed similar to the method of Porsolt et al. with modifications (Porsolt R D, Bertin A, Jalfre M. Behavioral despair in mice: a primary screening test for antidepressants. Arch Int Pharmacodyn Thér 1977; 229:327-36). In this paradigm, mice are forced to swim in an inescapable cylinder filled with water. Under these conditions, mice will initially try to escape and eventually develop immobility behavior; this behavior is interpreted as a passive stress-coping strategy or depression-like behavior. Swim tanks were positioned inside a box made of plastic. Each tank was separated from each other by opaque plastic sheets to the height of cylinders. Three mice were subjected to test at a time. Swim sessions were conducted for 6 min by placing mice in individual glass cylinders (46 cm height×20 cm diameter) containing water (20-cm deep, maintained at 24-25° C.). At this water level, the mouse tail does not touch the bottom of the container. The mouse was judged to be immobile whenever it remained floating passively without struggling in the water and only making those movements necessary to keep its nose/head above the water and to keep it afloat. The duration of immobility was evaluated during the total 6 min of the test and expressed as duration (sec) of immobility. Each mouse was tested only once. At the end of each session, mice were dried with a dry cloth and returned to their home cage placed on a thermal blanket to prevent hypothermia. Water was replaced after each trial. All testing sessions were recorded with a video camera (Sony Handicam, Model: DCR-HC38E; PAL) and scoring was done using the Forced Swim Scan, Version 2.0 software (Clever Systems Inc., Reston, Va., USA; see Hayashi E, Shimamura M, Kuratani K, Kinoshita M, Hara H. Automated experimental system capturing three behavioral components during murine forced swim test. Life Sci. 2011 Feb. 28; 88(9-10):411-7 and Yuan P, Tragon T, Xia M, Leclair C A, Skoumbourdis A P, Zheng W, Thomas C J, Huang R, Austin C P, Chen G, Guitart X. Phosphodiesterase 4 inhibitors enhance sexual pleasure-seeking activity in rodents. Pharmacol Biochem Behav. 2011; 98(3):349-55). For NCE testing: Test compound was administered in mice 15 min before swim session by i.v. route and immobility time was recorded for next 6 min. At the end of FST, the mouse were euthanized by rapid decapitation method and plasma and brain samples were collected and stored under −80° C. till further analysis. In the mouse forced swim assay, the compound of example 1 was dosed intravenously in a vehicle of 30% hydroxypropyl betacyclodextrin/70% citrate buffer pH 4 at a 5 mL/Kg dosing volume. The compound of example 10, P-1 demonstrated a statistically significant decrease in immobility time at 1 mg/Kg under these conditions. Drug levels were 207 nM in the plasma at this dose. The NR2B receptor occupancy was determined as reported above and was determined to be 69%.

It will be evident to one skilled in the art that the present disclosure is not limited to the foregoing disclosure and that it can be embodied in other specific forms without departing from the essential attributes thereof. It is therefore desired that the instant disclosure be considered in all respects as illustrative and not restrictive, reference being made to the appended claims, rather than to the foregoing disclosure, and all changes which come within the meaning and range of equivalency of the claims are therefore intended to be embraced therein.

We claim:
1. A compound of the formula I

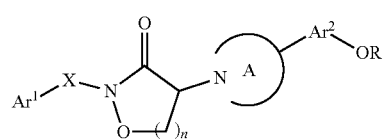

where:
Ar[1] is phenyl and is substituted with 0-3 substituent selected from cyano, halo, alkyl, haloalkyl and haloalkoxy;
Ar[2] is phenyl, pyridinyl or pyrimidinyl, and is substituted with 1 OR substituent and with 0-2 halo or alkyl substituents;
R is hydrogen or a prodrug moiety selected from the group consisting of alkyl esters, amino acid esters, alkoxy esters, phosphonic acids, phosphonic alkyl esters, alkoxyphosphononate acid, alkoxyphosphonate alkyl esters, alkyl carabamates, amino acid carbamates, alkyl phosporamidates, aryl phosphoramidates, and sulfamates;

X is a bond or $C_1$-$C_3$ alkylene;

n is 1 or 2;

ring A is piperidine or piperazine and is substituted with 0-1 halo substituents;

or a pharmaceutically acceptable salt thereof.

2. A compound of claim 1 where $Ar^1$ is phenyl and is substituted with 0-1 substituent selected from halo and alkyl; $Ar^2$ is phenyl, pyridinyl or pyrimidinyl, and is substituted with 1 OR substituent and with 0-2 halo or alkyl substituents; R is hydrogen; X is a bond or $C_1$-$C_3$ alkylene; n is 1 or 2; ring A is piperidine or piperazine and is substituted with 0-1 halo substituents; or a pharmaceutically acceptable salt thereof.

3. A compound of claim 2 where $Ar^1$ is phenyl and is substituted with 0-1 substituent selected from halo and alkyl; $Ar^2$ is phenyl or pyridinyl, and is substituted with 1 OR substituent and with 0-1 halo substituents; R is hydrogen; X is a methylene; n is 1 or 2; ring A is piperidine or piperazine and is substituted with 0-1 halo substituents; or a pharmaceutically acceptable salt thereof.

4. A compound of claim 1 where n is 1 and ring A is piperazine or piperidine substituted with 0-1 fluoro.

5. A compound of claim 1 where $Ar^1$ is phenyl substituted with 0-1 substituents selected from chloro, fluoro and methyl.

6. A compound of claim 1 where $Ar^2$ is selected from

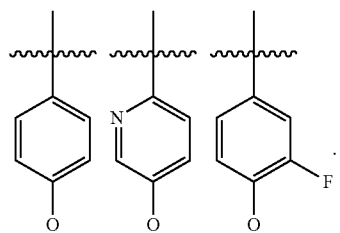

7. A compound of claim 1 where X is methylene.

8. A compound of claim 1 selected from the group consisting of

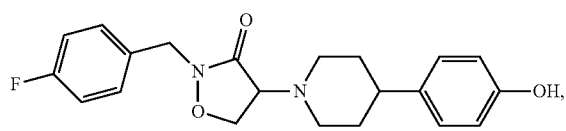

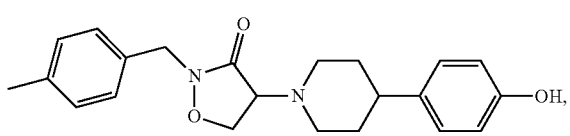

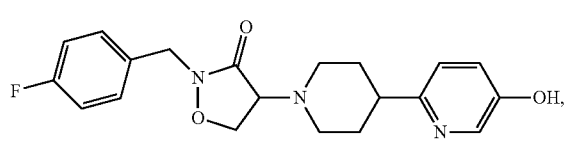

-continued

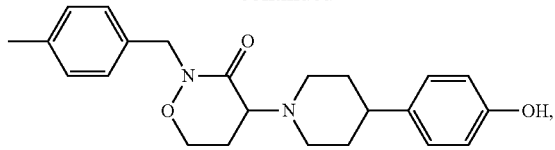

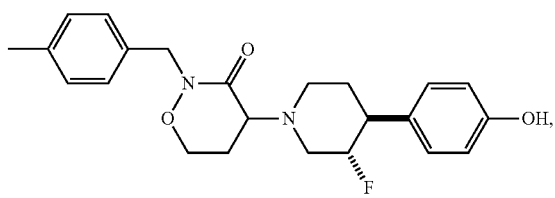

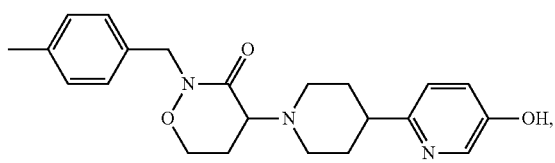

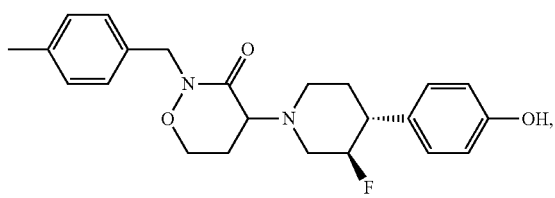

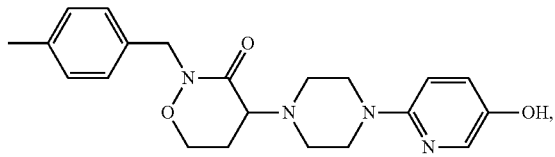

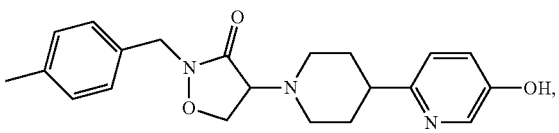

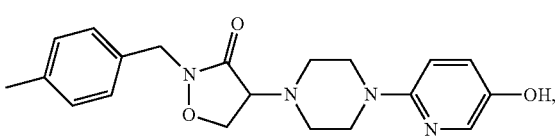

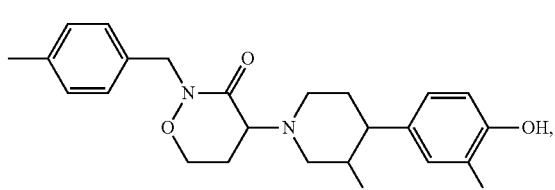

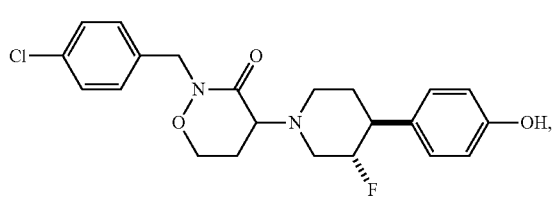

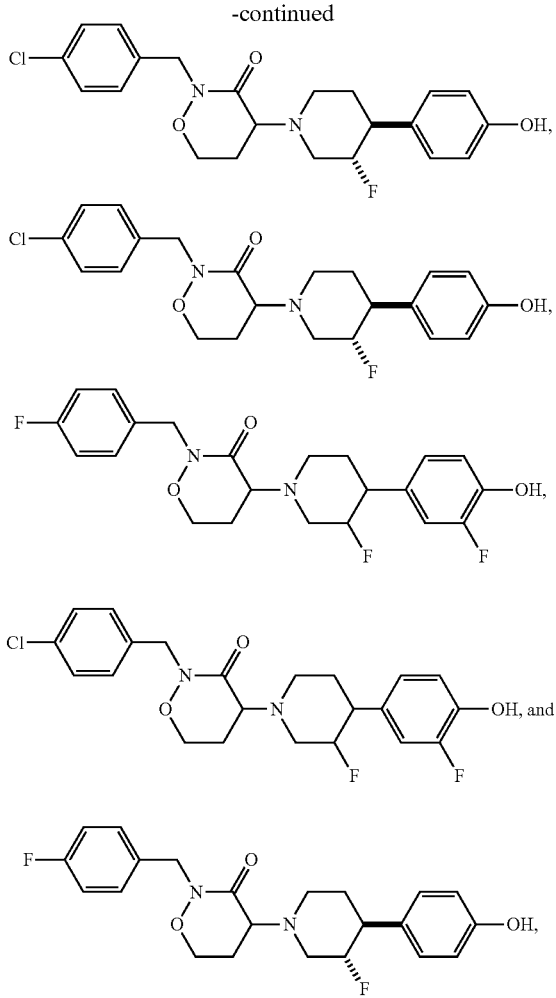

or a pharmaceutically acceptable salt thereof.

9. A pharmaceutical composition comprising a compound of claim 1 or a pharmaceutically acceptable salt thereof and a pharmaceutically acceptable carrier.

10. A method for the treatment of depression, Alzheimer's disease, neuropathic pain, or Parkinson's disease, which comprises administering to a patient a therapeutically effective amount of a compound of claim 1 or a pharmaceutically acceptable salt thereof.

11. The method of claim 10 directed to the treatment of depression.

12. The method of claim 10 directed to the treatment of Alzheimer's disease.

13. The method of claim 10 directed to the treatment of neuropathic pain.

14. A compound:

or a pharmaceutically acceptable salt thereof.

15. A pharmaceutical composition comprising a compound of claim 14 or a pharmaceutically acceptable salt thereof and a pharmaceutically acceptable carrier.

16. A method for the treatment of depression, Alzheimer's disease, neuropathic pain, or Parkinson's disease, which comprises administering to a patient a therapeutically effective amount of a compound of claim 14.

17. A compound:

or a pharmaceutically acceptable salt thereof

18. A pharmaceutical composition comprising a compound of claim 17 or a pharmaceutically acceptable salt thereof and a pharmaceutically acceptable carrier.

19. A method for the treatment of depression, Alzheimer's disease, neuropathic pain, or Parkinson's disease, which comprises administering to a patient a therapeutically effective amount of a compound of claim 17.

* * * * *